US012593819B2

(12) United States Patent
Li et al.

(10) Patent No.: US 12,593,819 B2
(45) Date of Patent: Apr. 7, 2026

(54) METHOD, APPARATUS AND SYSTEM FOR DETECTING CARBON EMISSION-INVOLVED GAS FROM RUMINANT

(71) Applicant: Intelligent Equipment Research Center, Beijing Academy of Agriculture and Forestry Sciences, Beijing (CN)

(72) Inventors: Bin Li, Beijing (CN); Wenwen Zhao, Beijing (CN); Haifeng Wang, Beijing (CN); Yuliang Zhao, Beijing (CN); Jun Zhu, Beijing (CN); Zejin Chen, Beijing (CN); Xuewen Liang, Beijing (CN); Lin Jiang, Beijing (CN)

(73) Assignee: Intelligent Equipment Research Center, Beijing Academy of Agriculture and Forestry Sciences, Beijing (CN)

( * ) Notice: Subject to any disclaimer, the term of this patent is extended or adjusted under 35 U.S.C. 154(b) by 369 days.

(21) Appl. No.: 18/195,397

(22) Filed: May 10, 2023

(65) Prior Publication Data

US 2024/0040995 A1     Feb. 8, 2024

(30) Foreign Application Priority Data

Aug. 8, 2022     (CN) .......................... 202210942086.4

(51) Int. Cl.
*A01K 5/02*          (2006.01)
*A01K 11/00*        (2006.01)
(Continued)

(52) U.S. Cl.
CPC .......... *A01K 5/0275* (2013.01); *A01K 11/004* (2013.01); *A01K 29/005* (2013.01);
(Continued)

(58) Field of Classification Search
None
See application file for complete search history.

(56) References Cited

U.S. PATENT DOCUMENTS 7,966,971 B2 *  6/2011  Zimmerman  ........ A01K 5/0225
                                                                     119/51.02
8,673,219 B2 *  3/2014  Caldeira  ................ A61B 5/082
                                                                     422/94

(Continued)

*Primary Examiner* — Hua Lu

(74) *Attorney, Agent, or Firm* — Patterson + Sheridan, LLP

(57)          ABSTRACT

A method, apparatus and system for detecting carbon emission-involved gas from a ruminant is provided, including: continuously receiving ear tag information of the ruminant in a monitoring range; determining an operation state of a feed supply system based on the ear tag information; and determining, based on collected emitted gas from the ruminant during eating, an emission rate of carbon emission-involved gas in the emitted gas when it is determined that the feed supply system is in a continuous operation state. In the method, apparatus and system, the ear tag information of the ruminant is detected to determine whether there is a ruminant in a detection area and feeding information of the ruminant, then the operation state of the feed supply system is controlled, and an intelligent information technology is used to acquire the emission rate of the carbon emission-involved gas matching the identity of the ruminant.

13 Claims, 11 Drawing Sheets

(51) Int. Cl.
    *A01K 29/00*     (2006.01)
    *G01N 33/00*     (2006.01)
    *G06T 7/73*     (2017.01)

(52) U.S. Cl.
    CPC ........... *G01N 33/0006* (2013.01); *G06T 7/73*
    (2017.01); *G06T 2207/10024* (2013.01); *G06T*
    *2207/10028* (2013.01); *G06T 2207/20081*
    (2013.01); *G06T 2207/20084* (2013.01)

(56) References Cited

U.S. PATENT DOCUMENTS

| | | | | |
|---|---|---|---|---|
| 2003/0084853 A1* | 5/2003 | Voogd | ................... | A01K 5/0275 |
| | | | | 119/51.02 |
| 2009/0288606 A1* | 11/2009 | Zimmerman | ........ | A01K 5/0225 |
| | | | | 119/51.01 |
| 2011/0192213 A1* | 8/2011 | Zimmerman | ........... | A01K 5/02 |
| | | | | 73/23.3 |
| 2011/0297090 A1* | 12/2011 | Chamberlain | ....... | A01K 5/0291 |
| | | | | 119/51.02 |
| 2012/0294876 A1* | 11/2012 | Zimmerman | ......... | A61B 5/082 |
| | | | | 128/203.14 |
| 2013/0061656 A1* | 3/2013 | Van Der Tol | ........ | A01K 29/005 |
| | | | | 73/23.3 |
| 2015/0302241 A1* | 10/2015 | Eineren | ................. | G06V 40/10 |
| | | | | 382/110 |
| 2015/0359199 A1* | 12/2015 | Schaefer | ............. | A01K 29/005 |
| | | | | 382/110 |
| 2017/0013802 A1* | 1/2017 | Zimmerman | ...... | G06K 7/10366 |
| 2019/0008124 A1* | 1/2019 | Komatsu | ............. | A01K 11/008 |
| 2019/0289826 A1* | 9/2019 | Tippery | ................ | G06N 20/20 |
| 2019/0380311 A1* | 12/2019 | Crouthamel | ......... | A01K 11/004 |
| 2021/0077555 A1* | 3/2021 | Machado | .............. | A61K 36/04 |
| 2021/0127630 A1* | 5/2021 | Zimmerman | .......... | G08C 17/00 |
| 2021/0148891 A1* | 5/2021 | Beal | ...................... | G06Q 50/02 |
| 2022/0276222 A1* | 9/2022 | Beal | ................... | G01N 33/0031 |
| 2023/0025459 A1* | 1/2023 | Laporte-Uribe | ..... | A61B 5/6861 |
| 2023/0136465 A1* | 5/2023 | Contreras | .............. | A23L 27/88 |
| | | | | 426/651 |
| 2023/0153752 A1* | 5/2023 | Allred | ............. | G06K 19/06028 |
| | | | | 705/28 |
| 2023/0225294 A1* | 7/2023 | Schaefer | ................ | A61B 5/015 |
| | | | | 340/573.3 |
| 2024/0257153 A1* | 8/2024 | Genzel | ................. | A61B 5/0205 |
| 2025/0005677 A1* | 1/2025 | Rapaport-Rom | ...... | G06Q 10/00 |
| 2025/0143261 A1* | 5/2025 | Zimmerman | ........ | A01K 5/0233 |

* cited by examiner

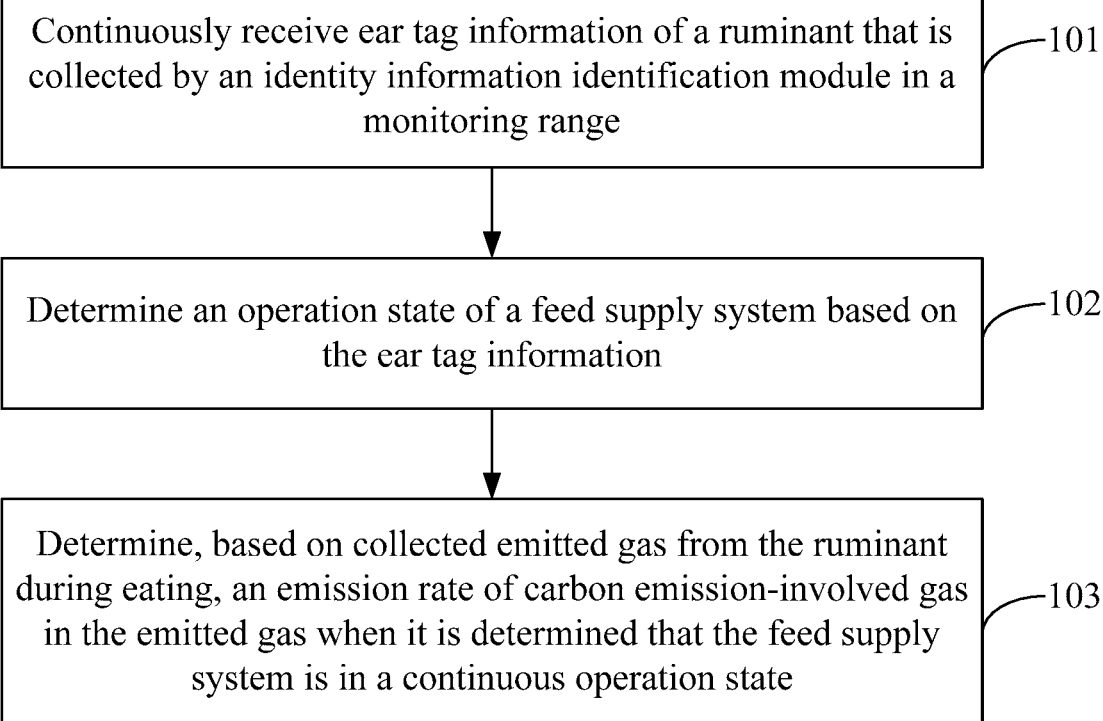

Continuously receive ear tag information of a ruminant that is collected by an identity information identification module in a monitoring range ⟶101

Determine an operation state of a feed supply system based on the ear tag information ⟶102

Determine, based on collected emitted gas from the ruminant during eating, an emission rate of carbon emission-involved gas in the emitted gas when it is determined that the feed supply system is in a continuous operation state ⟶103

FIG. 1

METHOD, APPARATUS AND SYSTEM FOR DETECTING CARBON EMISSION-INVOLVED GAS FROM RUMINANT

CROSS REFERENCE TO RELATED APPLICATION

This patent application claims the benefit and priority of Chinese Patent Application No. 202210942086.4 filed with the China National Intellectual Property Administration on Aug. 8, 2022, the disclosure of which is incorporated by reference herein in its entirety as part of the present application.

TECHNICAL FIELD

The present disclosure relates to the technical field of intelligent detection, and in particular, to a method, apparatus and system for detecting carbon emission-involved gas from a ruminant.

BACKGROUND

Gases such as $CO_2$ and $CH_4$ emitted by livestock in agriculture and animal husbandry become one of important sources of greenhouse gases. In particular, ruminants have a complex ruminant stomach system, and their rumen fermentation produces a large amount of $CH_4$ gas (which is 28 times that of $CO_2$ in causing greenhouse effect). According to statistics, ruminants in the world produce about 80 million tons of $CH_4$ per year, accounting for 28% of the amount of $CH_4$ released by global human activities. Therefore, it is of great significance to accurately monitor $CO_2$ and $CH_4$ generated by ruminants.

Currently, conventional methods such as an $SF_6$ tracing method, a $CO_2$ tracing method, a respiration chamber metabolism method, and related apparatuses such as a sniffer are mainly used to monitor an emission amount of carbon emission-involved gas from a ruminant, and usually have problems such as high labor intensity, complicated operation and low degree of automation, which seriously affects the effective measurement of the carbon emission.

Therefore, a method for monitoring a carbon emission amount from a ruminant under the condition of large-scale farming is provided, and can serve to effectively select livestock and poultry species with low carbon emission and select a feed combination with low carbon emission, and support the green development of animal husbandry.

SUMMARY

The present disclosure provides a method, apparatus and system for detecting carbon emission-involved gas from a ruminant, to solve the problems generally existing during monitoring of an emission amount of carbon emission-involved gas from a ruminant in the prior art, such as high labor intensity, complicated operation, low degree of automation and detection accuracy, and implement accurate and fully-automated detection of carbon emission-involved gas from a ruminant.

According to a first aspect, the present disclosure provides a method for detecting carbon emission-involved gas from a ruminant, including: continuously receiving ear tag information of the ruminant that is collected by an identity information identification module in a monitoring range; determining an operation state of a feed supply system based on the ear tag information; and determining, based on collected emitted gas from the ruminant during eating, an emission rate of carbon emission-involved gas in the emitted gas when it is determined that the feed supply system is in a continuous operation state.

In the method for detecting carbon emission-involved gas from a ruminant according to the present disclosure, the determining an operation state of a feed supply system based on the ear tag information includes: determining identity information of the ruminant based on the ear tag information; querying for a historical eating record of the ruminant from a target database based on the identity information; controlling the feed supply system to switch from a stop state to the continuous operation state so as to supply feed into a trough, if it is determined based on the historical eating record that the ruminant has not eaten within a first preset duration before a current moment; counting an operation duration of the feed supply system; controlling the feed supply system to switch from the continuous operation state to the stop state when it is determined that the operation duration has reached a second preset duration and/or the identity information identification module has not collected the ear tag information; and controlling the feed supply system to keep in the stop state if it is determined based on the historical eating record that the ruminant has eaten within the first preset duration before the current moment.

In the method for detecting carbon emission-involved gas from a ruminant according to the present disclosure, before the determining, based on collected emitted gas from the ruminant during eating, an emission rate of carbon emission-involved gas in the emitted gas, the method further includes: acquiring a plurality of depth image frames of the ruminant's head during eating collected by an RGB-D camera; inputting each depth image frame into a pre-trained target detection model to obtain a distribution feature map of feature points outputted by the target detection model; determining image coordinates of each feature point in each distribution feature map of the feature points, and converting the image coordinates of the feature point into spatial coordinates with the RGB-D camera as a coordinate origin, to obtain a feature point spatial coordinate data set, where the feature points include binaural feature points, binocular feature points and a mouth feature point of the ruminant; classifying, based on a support vector machine, spatial position relationships between all spatial coordinates in the feature point spatial coordinate data set and vent holes on the trough, and determining a head pose category of the ruminant relative to the trough; and marking effectiveness of the collected emitted gas based on the head pose category, where the vent holes are configured in the trough to collect the emitted gas.

In the method for detecting carbon emission-involved gas from a ruminant according to the present disclosure, the target detection model is obtained by training a basic network model by using a plurality of depth image samples of the ruminant's head and a distribution feature map label corresponding to each of the depth image samples; and the basic network model is generated based on ResNet as a basic network structure through replacing a classification layer of the ResNet with a deconvolution layer.

In the method for detecting carbon emission-involved gas from a ruminant according to the present disclosure, after the determining image coordinates of each feature point in each distribution feature map of the feature points, the method further includes:

determining, based on the image coordinates of each feature point, that a mouth of the ruminant is located in a current sampling area of the trough during eating, where the current sampling area includes a first sampling area and a second sampling area, and a distance between the first sampling area and each vent hole is less than that between the second sampling area and the vent hole; and marking effectiveness of the collected emitted gas based on the determined sampling area and the head pose category.

In the method for detecting carbon emission-involved gas from a ruminant according to the present disclosure, the head pose category includes forwardly facing the vent holes, laterally facing the vent holes, and eating with the head down; and the marking effectiveness of the collected emitted gas based on the determined sampling area and the head pose category includes: marking the emitted gas as effective when the current sampling area is the first sampling area; marking the emitted gas as effective if the head pose category is forwardly facing the vent holes when the current sampling area is the second sampling area; or marking the emitted gas as ineffective if the head pose category is laterally facing the vent holes or eating with the head down.

In the method for detecting carbon emission-involved gas from a ruminant according to the present disclosure, the determining, based on collected emitted gas from the ruminant during eating, an emission rate of carbon emission-involved gas in the emitted gas includes: acquiring a wind speed value in a main ventilation pipeline, a cross-sectional area of the main ventilation pipeline, and a gas temperature in the main ventilation pipeline, and acquiring a gas concentration value in the main ventilation pipeline, where the gas concentration value is measured by a gas sensor; and calculating the emission rate of the carbon emission-involved gas in the emitted gas based on the wind speed value, the cross-sectional area, the gas temperature, and the gas concentration value.

In the method for detecting carbon emission-involved gas from a ruminant according to the present disclosure, a calculation formula for calculating the emission rate of the carbon emission-involved gas in the emitted gas based on the wind speed value, the cross-sectional area, the gas temperature, and the gas concentration value is as follows:

$$m = \frac{V_t \times P_0 \times S \times C}{RT} \times \mu,$$

where in is the emission rate; $V_t$ is the wind speed value; $P_0$ is a standard atmospheric pressure; S is the cross-sectional area; C is the gas concentration value; R is a gas molar constant of the carbon emission-involved gas; T is an absolute temperature corresponding to the gas temperature; and $\mu$ is gas molar mass of the carbon emission-involved gas.

In the method for detecting carbon emission-involved gas from a ruminant according to the present disclosure, after the determining the emission rate of the carbon emission-involved gas in the emitted gas, the method further includes: acquiring emission rates collected at a plurality of sampling moments within a third preset duration; forming a coordinate point with each sampling moment and an emission rate collected at the sampling moment; determining a corresponding Bezier curve based on all coordinate points; and integrating emission rates of the Bezier curve within the third preset duration to obtain an emission amount of the carbon emission-involved gas in the emitted gas within the third preset duration.

The method for detecting carbon emission-involved gas from a ruminant according to the present disclosure further includes: acquiring emission amounts of carbon emission-involved gas acquired within a plurality of historical sampling durations, and acquiring parameters that are collected within each of the historical sampling durations and affect a carbon emission amount; training a pre-constructed multivariate regression prediction model with an emission amount collected in each historical sampling duration as a dependent variable and parameters corresponding to the historical sampling duration as independent variables, to obtain a carbon emission amount prediction model; and acquiring parameters that are acquired within any sampling duration and affect the carbon emission amount, and inputting the parameters into the carbon emission amount prediction model, to predict an emission amount within the sampling duration, where the parameters affecting the carbon emission amount include ruminant species information, feed type information, feed nutrient component information, and ruminant sign and body condition information.

In the method for detecting carbon emission-involved gas from a ruminant according to the present disclosure, after the acquiring parameters that are acquired within any sampling duration and affect the carbon emission amount, and inputting the parameters into the carbon emission amount prediction model, to predict an emission amount within the sampling duration, the method further includes: adjusting, if it is determined that the emission amount within the sampling duration is greater than a preset emission amount threshold, a feed type and/or feed nutrient components, and inputting adjusted feed type information, feed nutrient component information, ruminant species information and ruminant sign and body condition information into the carbon emission amount prediction model again to predict an adjusted emission amount within the sampling duration; and iteratively performing the above steps until it is determined that the adjusted emission amount within the sampling duration is less than or equal to the preset emission amount threshold.

In the method for detecting carbon emission-involved gas from a ruminant according to the present disclosure, before the determining the emission rate of the carbon emission-involved gas in the emitted gas, the method further includes: setting parameters of a robust filter to calibrate the gas sensor by using air collected when no ruminant eats.

According to a second aspect, the present disclosure further provides an apparatus for detecting carbon emission-involved gas from a ruminant, including: a data acquisition unit, configured to continuously receive ear tag information of the ruminant that is collected by an identity information identification module in a monitoring range; an operation control unit, configured to determine an operation state of a feed supply system based on the ear tag information; and an emission rate detection unit, configured to determine, based on collected emitted gas from the ruminant during eating, an emission rate of carbon emission-involved gas in the emitted gas when it is determined that the feed supply system is in a continuous operation state.

According to a third aspect, the present disclosure provides a system for detecting carbon emission-involved gas from a ruminant, including an identity information identification module, a feed supply system, a gas guiding system, and a gas analysis system, where the feed supply system includes a trough and a quantitative feeder, where an output end of the quantitative feeder is connected to the trough through a discharge pipe, and a side edge of the trough is provided with vent holes; the gas guiding system includes a main ventilation pipeline and a sampling pipeline; an air inlet end of the main ventilation pipeline is connected to the vent holes of the trough, and a fan is arranged in the main ventilation pipeline; and when the fan is running, negative pressure is formed in the main ventilation pipeline, so as to guide gas at the vent holes of the trough into the main ventilation pipeline; the sampling pipeline is in connection with the main ventilation pipeline and the gas analysis system to sample the gas in the main ventilation pipeline to the gas analysis system; the gas analysis system includes a gas sensor; and the system further includes a processor; and the processor includes the apparatus for detecting carbon emission-involved gas from a ruminant according to the second aspect.

According to a fourth aspect, the present disclosure provides an electronic device, including a memory, a processor, and a computer program stored in the memory and executable on the processor, where the computer program, when executed by the processor, implements the method for detecting carbon emission-involved gas from a ruminant according to any one of the above aspects.

According to a fifth aspect, the present disclosure further provides a non-transient computer-readable storage medium storing a computer program thereon, wherein the computer program, when executed by the processor, implements the method for detecting carbon emission-involved gas from a ruminant according to any one of the above aspects.

In the method, apparatus and system for detecting carbon emission-involved gas from a ruminant according to the present disclosure, the ear tag information of the ruminant is detected to determine whether there is a ruminant in a detection area and feeding information of the ruminant, then the operation state of the feed supply system is controlled, and an intelligent information technology is used to acquire the emission rate of the carbon emission-involved gas matching the identity of the ruminant, which can detect the carbon emission-involved gas amount from the ruminant by means of flexible manpower.

BRIEF DESCRIPTION OF THE DRAWINGS

To describe the technical solutions in the present disclosure or in the prior art more clearly, the following briefly describes the accompanying drawings required for describing the embodiments or the prior art. Apparently, the accompanying drawings in the following description show some embodiments of the present disclosure, and a person skilled in the art may still derive other accompanying drawings from these accompanying drawings without creative efforts.

FIG. 1 is a first schematic flowchart of a method for detecting carbon emission-involved gas from a ruminant according to the present disclosure;

6

Figure 6:
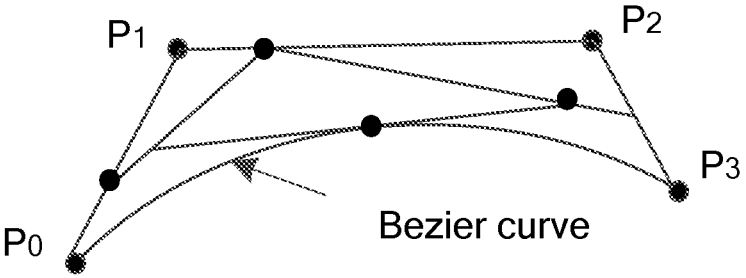
Figure 7:
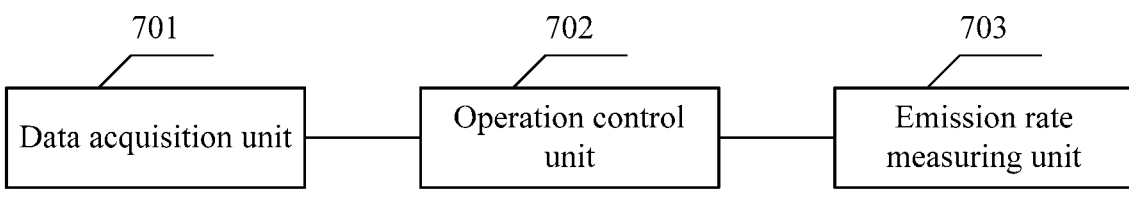
Figure 8:
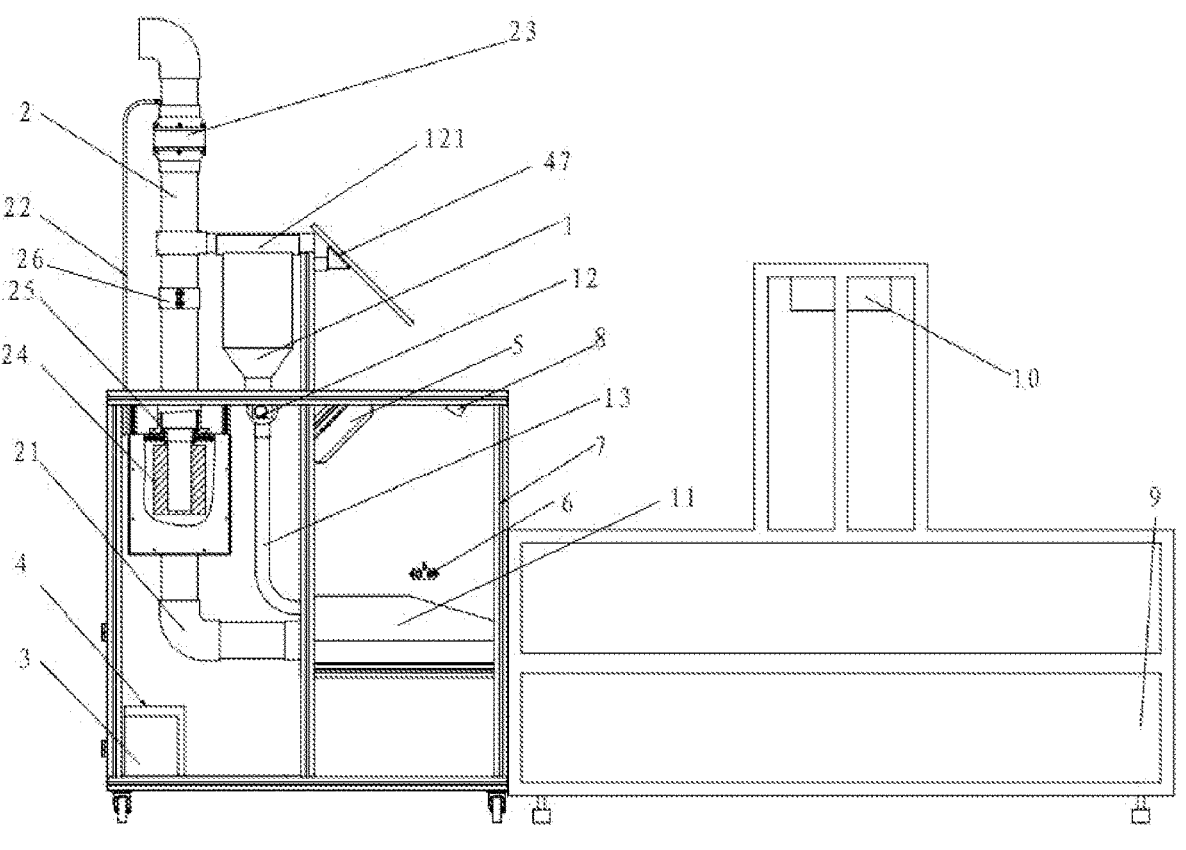
Figure 9:
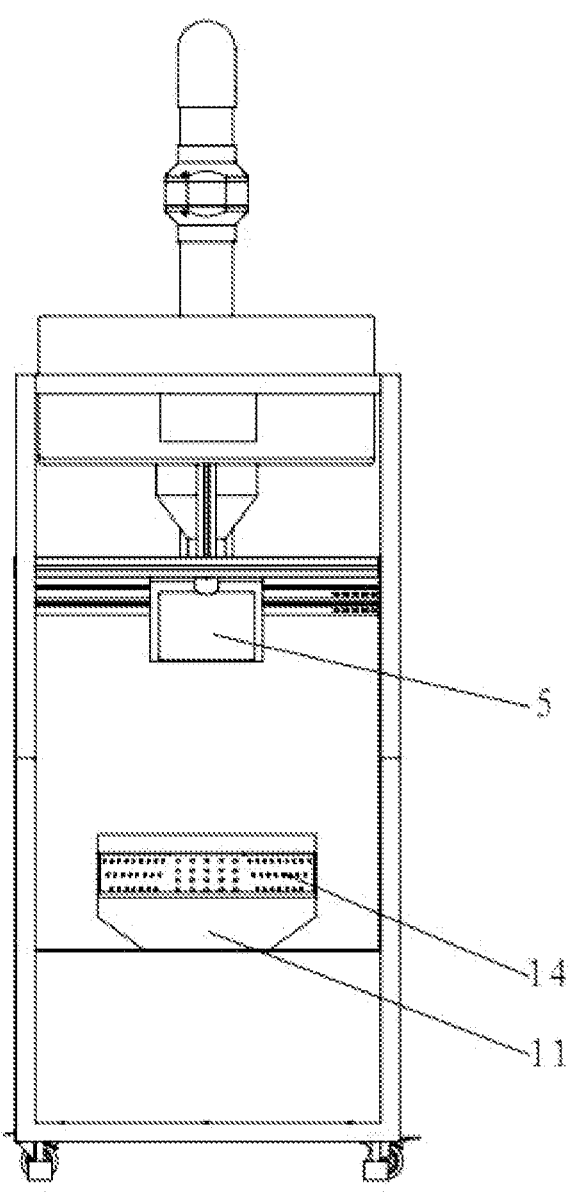
Figure 10:
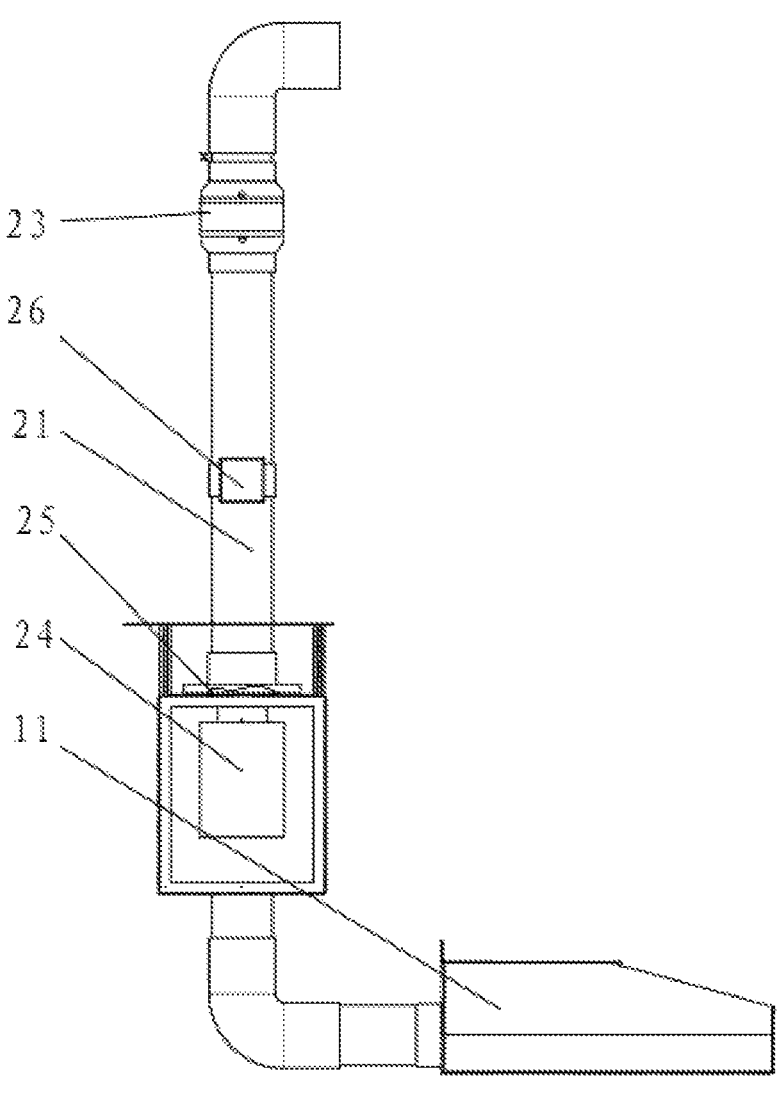
Figure 11:
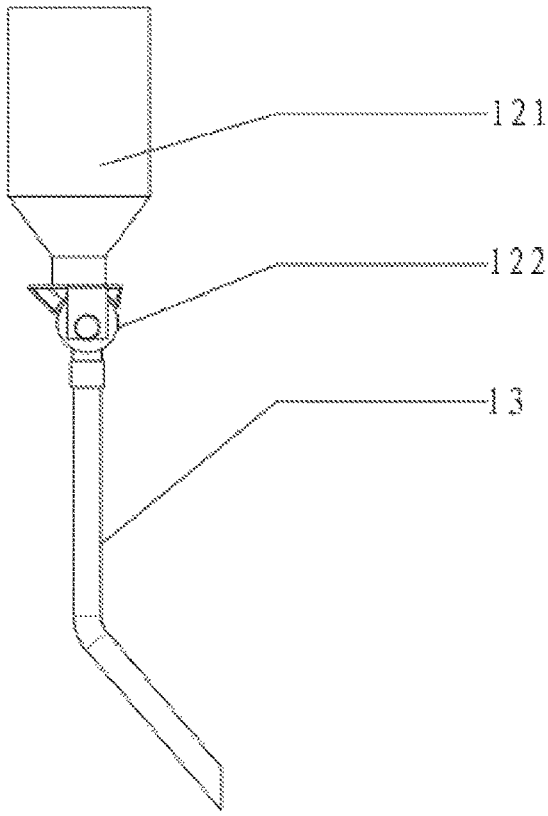
Figure 12:
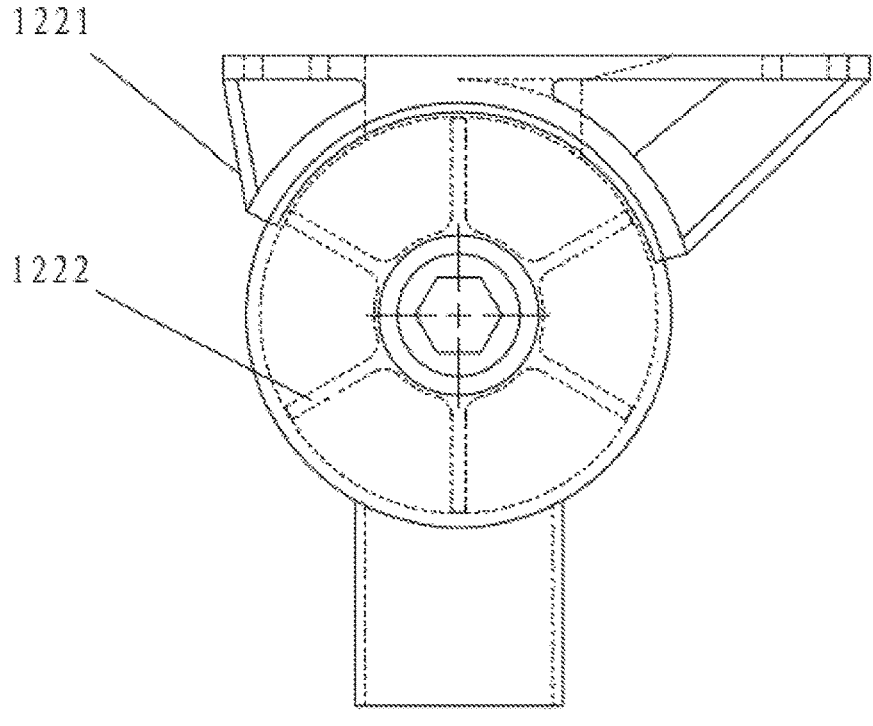
Figure 13:
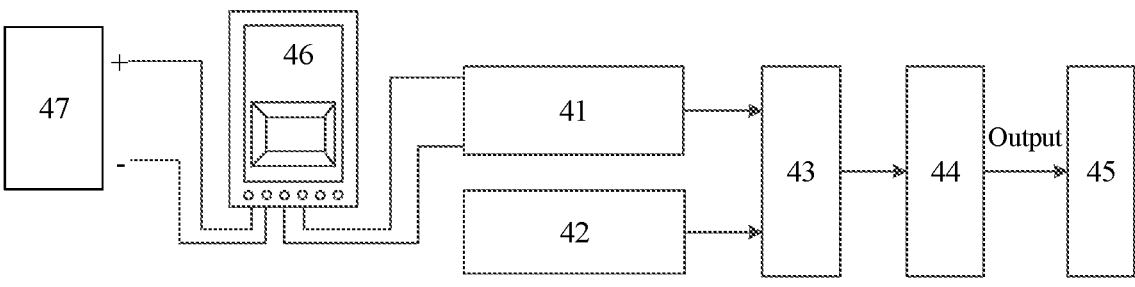
Figure 14:
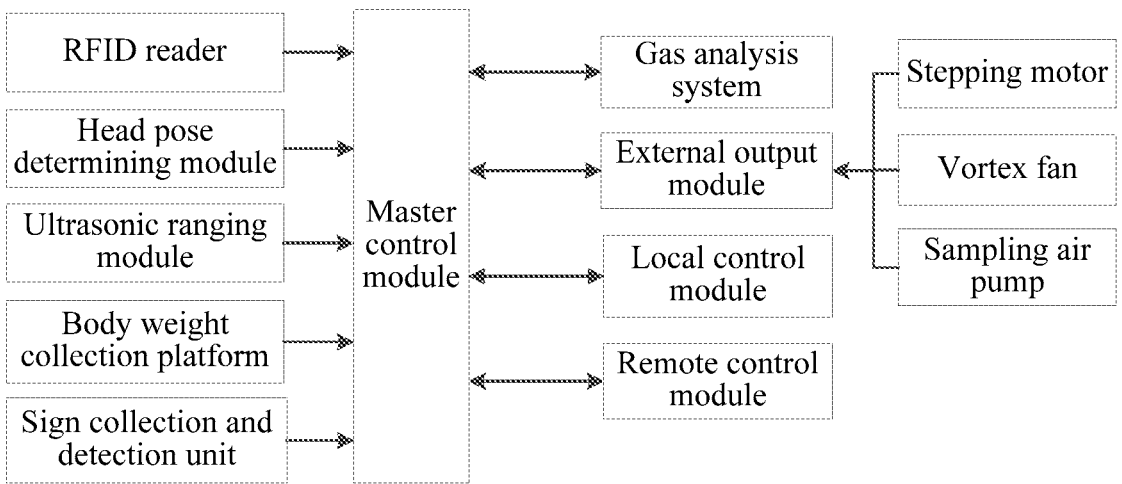
Figure 15:
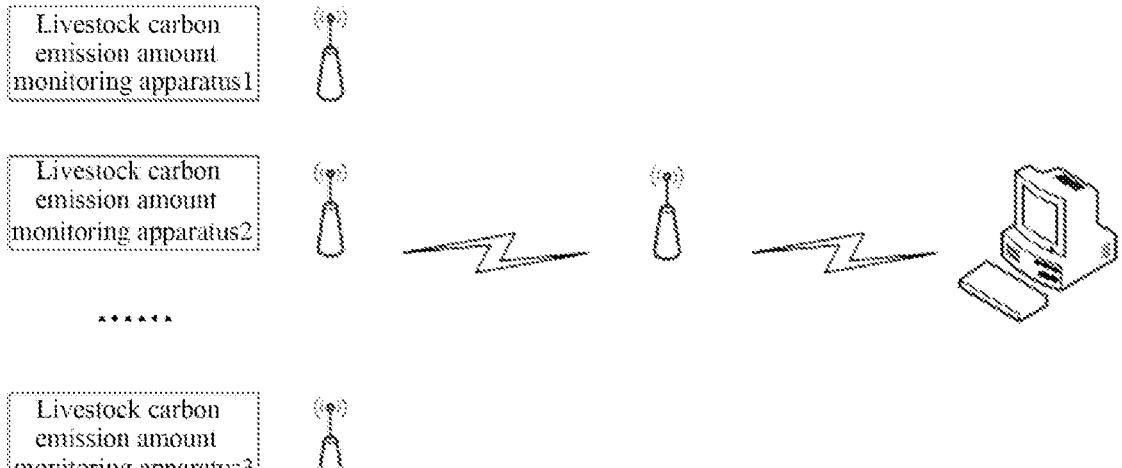
Figure 16:
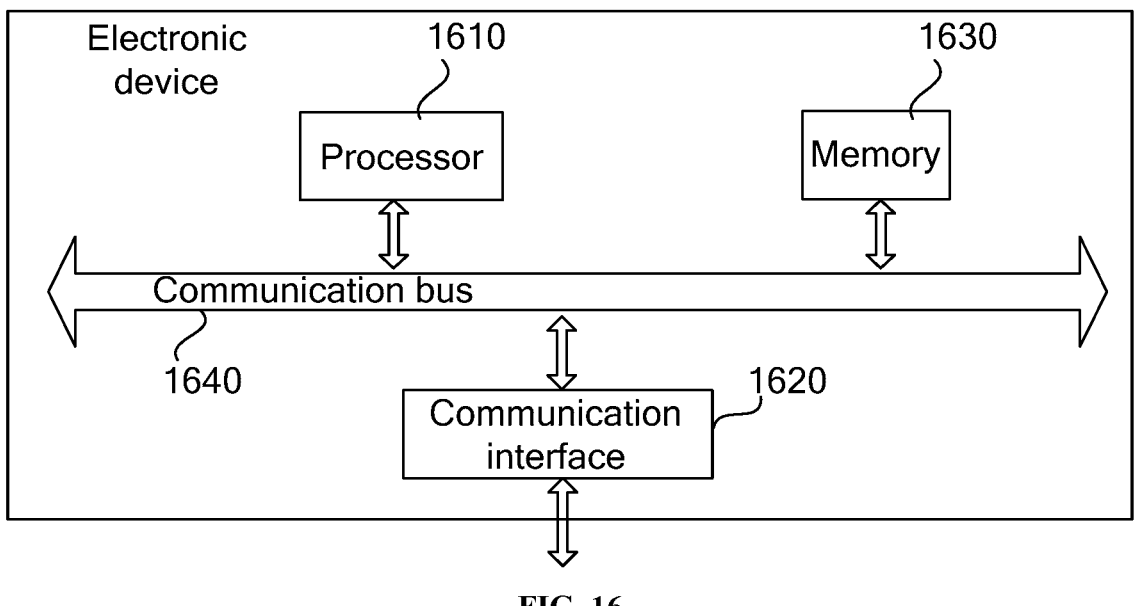

FIG. 6 is a schematic diagram of determining a Bezier curve based on emission rates collected at four sampling moments according to the present disclosure;

FIG. 7 is a schematic structural diagram of an apparatus for monitoring a carbon emission amount from a ruminant according to the present disclosure;

FIG. 8 is a front view of an apparatus for monitoring a carbon emission amount from a ruminant according to the present disclosure;

FIG. 9 is a left view of an apparatus for monitoring a carbon emission amount from a ruminant according to the present disclosure;

FIG. 10 is a schematic structural diagram of relevant components of a main ventilation pipeline in a gas guiding system according to the present disclosure;

FIG. 11 is a partial schematic structural diagram of a quantitative feeder according to the present disclosure;

FIG. 12 is a schematic structural diagram of a discharger according to the present disclosure;

FIG. 13 is a schematic structural diagram of a power supply system according to the present disclosure;

FIG. 14 is a schematic diagram showing a connection between a main control module and other components according to the present disclosure;

FIG. 15 is a schematic structural diagram of a system for monitoring a carbon emission amount from a ruminant according to the present disclosure; and FIG. 16 is a schematic structural diagram of an electronic device according to the present disclosure.

Reference numerals in the accompanying drawings are as follows:

1: Feed supply system; 2. Gas guiding system; 3. Gas analysis system; 4: Power supply system; 5: Radio frequency identification (RFID) reader; 6. Ultrasonic ranging module; 7: Main body structure; 8: Visual system; 9: Body weight collection platform; 10. Sign collection and detection unit; 11: Trough; 12: Quantitative feeder; 13: Discharge pipe; 14: Vent hole; 21: Main ventilation pipeline; 22: Sampling pipeline; 23: Fan; 24: First air filter; 25: Perforated plate; 26: Wind speed sensor; 121: Feed box; 122: Discharger; 1221: Discharger housing; 1222: Distributing gear teeth; 41: Storage battery; 42: Switching power supply; 43: Power switching module; 44: Power conversion module; 45: Power consumption unit; 46: Solar charging controller; 47: Solar cell panel.

DETAILED DESCRIPTION OF THE EMBODIMENTS

To make the objectives, technical solutions and advantages of the present disclosure clearer, the following clearly and completely describes the technical solutions in the present disclosure with reference to the accompanying drawings in the present disclosure. Apparently, the described embodiments are some but not all of the embodiments of the present disclosure. All other embodiments obtained by a person of ordinary skill in the art based on the embodiments of the present disclosure without creative efforts shall fall within the protection scope of the present disclosure.

It should be noted that in the description of the embodiments of the present disclosure, terms "including", "comprising" or any other variants thereof are intended to cover non-exclusive inclusion, so that a process, method, article or device including a series of elements includes not only those elements but also other elements not explicitly listed, or elements inherent to such a process, method, article, or device. Without more restrictions, the elements defined by the sentence "including a . . . " do not exclude the existence of other identical elements in a process, method, article, or device including the elements. An orientation or positional relationship indicated by a term such as "upper" or "lower" is based on the orientation or positional relationship shown in the accompanying drawings, which is only for convenience of describing the present disclosure and simplifying the description, rather than indicating or implying that the apparatus or element referred to must have a particular orientation and be constructed and operated in a particular orientation, and therefore should not be construed as limiting the present disclosure. Unless otherwise clearly specified and limited, terms such as "mounted", "connected with" and "connected to" should be understood in a broad sense. For example, the term may be a fixed connection, a detachable connection or an integral connection; may be a mechanical connection or an electrical connection; and may be a direct connection, an indirect connection by means of an intermediate medium, or internal communication between two elements. A person of ordinary skill in the art may understand specific meanings of the above terms in the present disclosure based on a specific situation.

The terms such as "first" and "second" in the present application are used to distinguish between similar objects and are not intended to describe a specific order or sequence. It should be understood that data used in such a way may be interchanged under appropriate circumstances so that the embodiments of the present application can be implemented in an order other than those illustrated or described herein, the objects distinguished by "first", "second", etc. are usually of one type, and the number of objects is not limited. For example, one or more first objects may be provided. In addition, "and/or" means at least one of the connected objects, and the character "/" generally indicates an "or" relationship between associated objects.

A method, apparatus and system for detecting carbon emission-involved gas from a ruminant according to embodiments of the present disclosure are described below with reference to FIGS. 1-16.

FIG. 1 is a first schematic flowchart of a method for detecting carbon emission-involved gas from a ruminant according to the present disclosure, which as shown in FIG. 1, may be performed by a controller of an apparatus for detecting carbon emission-involved gas from a ruminant, and includes but not limited to the following steps 101-103.

In step 101, the controller continuously receives ear tag information collected by an identity information identification module from the ruminant in a monitoring range.

The ruminant may include an animal such as dairy cattle/beef cattle or sheep. During breeding of such animals, an ear tag is usually mounted on the body (such as the ear) of the ruminant to store ear tag information of the ruminant, such as an animal species, identity information (such as unique identity number), and breeding information during breeding, which is not specifically limited by the present disclosure.

According to the present disclosure, a fixedly arranged RFID sensor reads the ear tag of the ruminant entering a monitoring range of the RFID sensor, to obtain the corresponding ear tag information.

In step 102, the controller determines an operation state of a feed supply system based on the ear tag information.

To facilitate the description of the method for detecting carbon emission-involved gas from a ruminant according to the present disclosure, the following description will be made with cattle as an example of the ruminant.

After acquiring the ear tag information of any cattle (hereinafter referred to as a target cattle) entering the monitoring range, the controller can know that there is a cattle entering the periphery of the apparatus for detecting carbon emission-involved gas from a ruminant.

Further, based on the ear tag information, it can be determined whether the target cattle has eaten within a certain period of time (feeding cycle), and then the operation state of the feed supply system is determined.

Optionally, the feed supply system includes a trough and a quantitative feeder, where an output end of the quantitative feeder is connected to the trough through a discharge pipe.

The operation state of the feed supply system mainly includes a stop state and a continuous operation state. The stop state refers to a state in which a quantitative feeder is stopped, and does not put feed in a feed box into the trough; and the continuous operation state refers to a state in which the quantitative feeder puts the feed in the feed box into the trough in a preset mode.

For example, when the target cattle enters the monitoring range of the RFID sensor (equivalent to the periphery of the apparatus for detecting carbon emission-involved gas from a ruminant), the RFID sensor feeds back the detected ear tag information to the controller; and based on the ear tag information, the controller determines that the target cattle may be fed, and the feed supply system is controlled to be in the continuous operation state.

Optionally, the feed supply system may continuously put the feed in the feed box into the trough, or may perform continuous operation in such a preset mode that each feeding is performed for $t_1$ (e.g., 20 s) and then is stopped for $t_2$ (e.g., 30 s). It should be noted that the above preset mode may be implemented through controlling a drive (such as a stepping motor) of the feed supply system by the controller based on an actual demand.

In step 103, when it is determined that the feed supply system is in a continuous operation state, an emission rate of carbon emission-involved gas in the emitted gas is determined based on collected emitted gas from the ruminant during eating.

A side edge of the above trough is provided with vent holes. According to the present disclosure, after it is determined that the feed supply system is in the continuous operation state, the emitted gas from the target cattle during eating is collected from the vent holes by controlling an action of a gas guiding system.

Optionally, the above gas guiding system mainly includes a main ventilation pipeline and a sampling pipeline; an air inlet end of the main ventilation pipeline is connected to the vent holes of the trough, and a fan is arranged in the main ventilation pipeline; when the fan is running, negative pressure is formed in the main ventilation pipeline, so that the emitted gas from the target cattle during eating and collected at the vent holes of the trough can be introduced into the main ventilation pipeline. The sampling pipeline is in communication connection with the main ventilation pipeline and a gas analysis system, and thus the gas in the main ventilation pipeline can be sampled to the gas analysis system (mainly including a gas sensor). Finally, the gas analysis system measures the concentration of the carbon emission-involved gas in the emitted gas, and then calculates the emission rate of the carbon emission-involved gas in the emitted gas.

It should be noted that if the RFID sensor does not detect the ear tag information, the controller does not drive the feed supply system to act, that is, the feed supply system is in the stop state, and in this case, the content of the carbon emission-involved gas in the collected emitted gas is not detected, or even if the content of the carbon emission-involved gas is detected, a detection result is not recorded.

In the method for detecting carbon emission-involved gas from a ruminant according to the present disclosure, the ear tag information of the ruminant is detected to determine whether there is a ruminant in a detection area and feeding information of the ruminant, then the operation state of the feed supply system is controlled, and by an intelligent information technology, the emission rate of the carbon emission-involved gas matching the identity of the ruminant is acquired, which can detect an amount of the carbon emission-involved gas from the ruminant by means of flexible manpower.

Based on the content of the above embodiment, in an optional embodiment, the determining an operation state of a feed supply system based on the ear tag information includes: determining identity information of the ruminant based on the ear tag information; querying for a historical eating record of the ruminant from a target database based on the identity information; controlling the feed supply system to switch from a stop state to the continuous operation state so as to supply feed into a trough, if it is determined based on the historical eating record that the ruminant has not eaten within a first preset duration before a current moment; counting an operation duration of the feed supply system; controlling the feed supply system to switch from the continuous operation state to the stop state when it is determined that the operation duration has reached a second preset duration and/or the identity information identification module has not collected the ear tag information; and controlling the feed supply system to keep in the stop state if it is determined based on the historical eating record that the ruminant has eaten within the first preset duration before the current moment.

Specifically, the present disclosure provides a specific implementation of determining an operation state of a feed supply system based on the ear tag information, including the following steps.

First, identity information of a target cattle is determined based on ear tag information of the target cattle collected by the RFID sensor, and the identity information may be a unique identity number of the target cattle (such as XX001).

Further, a target database is pre-constructed in the present disclosure, the identity number of each cattle is pre-stored in the target database, historical eating information of the cattle corresponding to each identity number is recorded, for example, "XX002, 20220715, 8:20, 12:30, 15:10", and the eating information indicates that the cattle with the identity number XX002 has eaten three times on Jul. 15, 2022 at times of 8:20, 12:30, and 15:10, respectively.

It should be noted that the above process of constructing the target database includes: collecting, by means of the RFID sensor, the ear tag information of any cattle eating near the apparatus for detecting carbon emission-involved gas from a ruminant, recording its eating time to generate a new piece of eating information; and using the generated new eating information to update original eating information corresponding to the identity information of the cattle in the target database.

It should be noted that the above first preset duration may be comprehensively set by a user based on an actual situation with reference to requirements for a feeding cycle of cattle and eating rules of the cattle.

According to the present disclosure, after the identity information of the target cattle is acquired, the target database is queried for information, and if it is queried from the target database based on the identity information that the target cattle has not eaten within a duration before the current moment, the controller controls the feed supply system to switch from the stop state to the continuous operation state, that is, controls the driving action (such as the stepping motor) of the feed supply system.

In the method for detecting carbon emission-involved gas from a ruminant according to the present disclosure, in order to avoid a case in which a single cattle comes to the trough for many times within the first preset duration for eating, if it is queried from the target database that the target cattle has eaten within the first preset duration, the feed supply system continues keeping in the stop state, that is, no feed is putted into the trough. In this way, the target cattle leaves the apparatus for detecting carbon emission-involved gas from a ruminant when no feed is putted into, and other cattle can continue to enter the monitoring range.

Further, if the identity information of the target cattle cannot be found from the target database, a piece of new identity information can be directly created for the target cattle in the target database, and the current moment is set as the time when the target cattle eats for the first time.

Further, in the method for detecting carbon emission-involved gas from a ruminant according to the present disclosure, in order to prevent a single cattle from continuously eating at the trough for a long time in a single time, when the identity information of the target cattle is detected within continuous second preset durations, that is, the continuous operation duration of the feed supply system reaches the second preset duration, the feed supply system is controlled to switch from the continuous operation state to the stop state, that is, to stop feeding into the trough. When no feed is putted into, the target cattle leaves the apparatus for detecting carbon emission-involved gas from a ruminant, and other cattle can continue to enter the monitoring range.

Further, in the method for detecting carbon emission-involved gas from a ruminant according to the present disclosure, if the RFID sensor loses the identity information of the detected target cattle during the feeding by the continuous operation of the feed supply system, it indicates that the target cattle has left, and in this case, the feed supply system is controlled to switch from the continuous operation state to the stop state, that is, to stop feeding into the trough.

In the method for detecting carbon emission-involved gas from a ruminant according to the present disclosure, the feeding state of the feed supply system can be determined with reference to the identity information in the ear tag information detected by the RFID sensor, so that different cattle can be automatically induced to eat, and the eating duration of cattle can be controlled by means of the feed feeding duration, thereby setting the detection duration for each cattle. Due to the diversity and comprehensiveness of detected objects, the detection accuracy of the emission rate of the carbon emission-involved gas in the emitted gas can be effectively improved.

Based on the content of the above embodiment, in an optional embodiment, before the determining, based on collected emitted gas from the ruminant during eating, an emission rate of carbon emission-involved gas in the emitted gas, the method further includes: acquiring a plurality of depth image frames of the ruminant's head during eating collected by an RGB-D camera; inputting each depth image frame into a pre-trained target detection model to obtain a distribution feature map of feature points outputted by the target detection model; determining image coordinates of each feature point in each distribution feature map of the feature points, and converting the image coordinates of the feature point into spatial coordinates with the RGB-D camera as a coordinate origin, to obtain a feature point spatial coordinate data set, where the feature points include binaural feature points, binocular feature points and a mouth feature point of the ruminant; classifying, based on a support vector machine, spatial position relationships between all spatial coordinates in the feature point spatial coordinate data set and vent holes in the trough, and determining a head pose category of the ruminant relative to the trough; and marking effectiveness of the collected emitted gas based on the head pose category, where the vent holes are configured in the trough to collect the emitted gas.

When the target cattle is eating, its head pose is an important influencing factor for detecting the content of the carbon emission-involved gas in the emitted gas generated during eating. Generally, based on the head pose of the target cattle, when it is determined that the mouth (snout) of the target cattle that emits the gas is closer to the vent holes located in the trough, the content of the carbon emission-involved gas in the emitted gas collected from the vent holes is closer to a true value; and when it is determined that the mouth of the target cattle that emits the gas is farther from the vent holes, the detected content of the carbon emission-involved gas in the emitted gas has a greater error, or may even be used as ineffective data.

Figure 2:
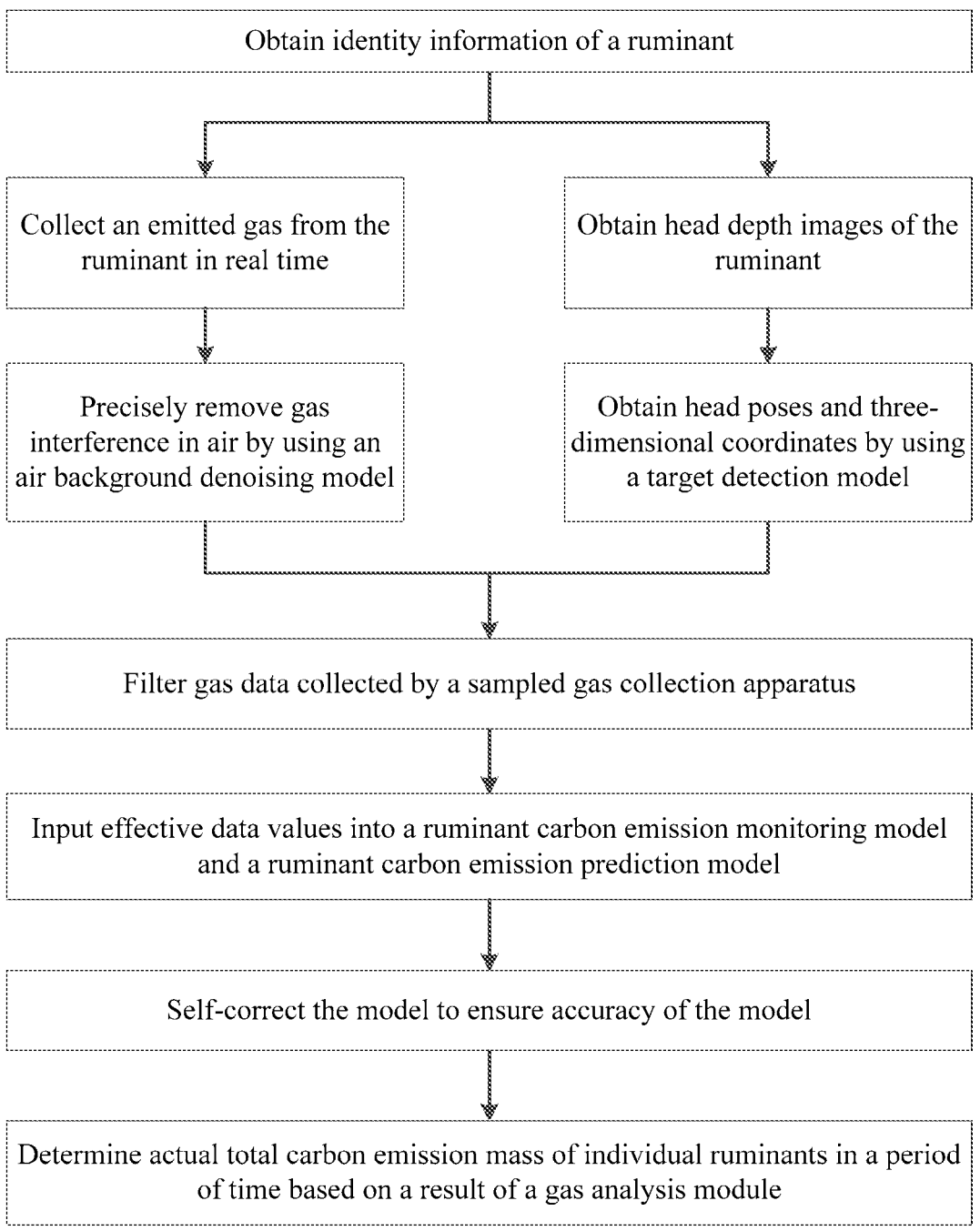
FIG. 2 is a second schematic flowchart of a method for detecting carbon emission-involved gas from a ruminant according to the present disclosure.

FIG. 2 is a second schematic flowchart of a method for detecting carbon emission-involved gas from a ruminant according to the present disclosure. As shown in FIG. 2, according to the present disclosure, depth images of a target cattle's head are collected in real time by using an RGB-D camera arranged around while an emitted gas from the target cattle is collected at vent holes in the trough by using a gas guiding system, so as to determine a head pose of the target cattle based on the depth images. The head pose is positioned mainly by using three-dimensional spatial position coordinates of a plurality of key points of the head.

Specifically, a DeepLabCut algorithm model is used as a target detection model in advance to obtain three-dimensional spatial position coordinates of key points of the head of the target cattle.

In an optional embodiment, the target detection model is obtained by training a basic network model by using a plurality of depth image samples of the ruminant's head and a distribution feature map label corresponding to each of the depth image samples.

The basic network model is generated based on ResNet as a basic network structure through replacing a classification layer of ResNet with a deconvolution layer.

Specifically, the DeepLabCut algorithm model is a deep convolutional network structure that combines object recognition and semantic segmentation algorithms. In the present application, an example in which ResNet is used as the basic network structure of the DeepLabCut algorithm model is described.

Based on the original basic network structure ResNet, a classification layer of the network structure of ResNet is removed, and a deconvolution layer for up-sampling is introduced to substitute for the classification layer of ResNet, for up-sampling.

According to the present disclosure, after any depth image frame is inputted into the target detection model, the deconvolution layer is connected to ResNet for up-sampling, so that a distribution feature map containing the distribution of feature points can be obtained.

As for the pose detection of the cattle's head, the above feature points may include binaural feature points, binocular feature points, and a mouth feature point. That is, with depth images of the head as an input of the target detection model according to the present disclosure, feature extraction is performed by means of the ResNet model with the classification layer removed, and then the deconvolution layer is used for up-sampling, so that the distribution of the above five feature points on the distribution feature map can be obtained.

Further, specific positions of the above feature points in the distribution feature map are determined based on a probability density state and a vector trend of the feature points in the distribution feature map, thereby obtaining image coordinates of the feature points.

After the image coordinates of the feature points on the distribution feature map are obtained by using the above steps, three-dimensional spatial coordinates (hereinafter referred to as three-dimensional coordinates or spatial coordinates) of each feature point can be obtained by converting the image coordinates on the distribution feature map into world coordinates.

In an optional embodiment, the present disclosure provides a method for converting image coordinates on the distribution feature map into world coordinates with an RGB-D camera as an origin, through conversion formulas as follows:

$$\begin{cases} X = \dfrac{(u - c_x) * d_{(u,v)}}{f_x} \\ Y = \dfrac{(v - c_y) * d_{(u,v)}}{f_y} \\ Z = d_{(u,v)} \end{cases};$$

$$f_x = f/d_x; \text{ and}$$

$$f_y = f/d_y,$$

where $(u, v)$ is image coordinates of any feature point on the distribution feature map; $c_x$ and $c_y$ represent the number of pixels in a central X-axis and the number of pixels in a central Y-axis on the distribution feature map, respectively; $d_x$ and $d_y$ are actual physical sizes of a pixel on a photosensitive chip of the RGB-D camera, respectively; $d_{(u,v)}$ is a depth value of the any feature point; $f_x$ and $f_y$ are pixel focal lengths of the RGB-D camera; and $f$ is a physical focal length of the RGB-D camera.

In this way, by inputting each depth image frame of the target cattle's head into the trained target detection model, the image coordinates of each feature point distributed in the distribution feature map are obtained, and then the spatial coordinates of each feature point are obtained through coordinate transformation, so that the head pose category of the target cattle relative to the trough can be determined based on a spatial distribution state of all feature points, and then whether the emitted gas collected at this moment is effective can be determined based on the head pose category of the target cattle relative to the trough.

Specifically, according to the present disclosure, by data query and related investigation on the head pose of the ruminant during eating, there are mainly three head pose categories of the ruminant based on the head's depth images, i.e., forwardly facing an air inlet of the trough, laterally facing the air inlet of the trough, and eating with the head down.

The characteristics of the three head poses are as shown in Table 1 below.

TABLE 1

| Definition of three head pose categories | |
| --- | --- |
| Head pose | Definitions |
| Forwardly facing vent holes of the trough | The head is in the trough, and the ears, the eyes and the mouth forwardly face the vent holes. |
| Laterally facing the vent holes of the trough | The head is in the trough, and the ears, the eyes and the mouth laterally face the vent holes. |
| Eating with the head down | The head is in the trough, and the ears, the eyes and the mouth face the bottom of the trough. |

A relative position relationship between the vent holes in a side wall of the trough and the ears, the eyes and the mouth can be comprehensively determined by means of the spatial coordinates of five feature points, i.e., the binaural feature points, the binocular feature points and the mouth feature point, an spatial area coordinate of an area where the trough is located, and spatial coordinates of the vent holes.

In order to accurately detect the carbon emission-involved gas in the emitted gas from the target cattle, the measurement needs to be performed in a pose state in which the target cattle forwardly faces the air inlet of the trough. However, in an actual situation, it is found that due to the different head pose categories of a target cattle, large errors may occur to the measurement under some categories.

In order to overcome the impact of the head pose category on the detection result, according to the present disclosure, a plurality of depth image frames of the target cattle's head are collected within a very short duration (e.g., within 1 second) during the same eating, then a plurality of groups of feature point spatial coordinate data are obtained to construct a feature point spatial coordinate data set, and then support vector classification (SVC) is used as a classifier to perform head pose classification on spatial position relationships between spatial coordinates of all feature points in the feature point spatial coordinate data set and the vent holes in the trough.

The head pose classification results of the feature point spatial coordinate data set mainly fall into three categories: the head forwardly facing the air inlet of the trough, the head laterally facing the air inlet of the trough, and eating with the head down.

It should be noted that before the head pose classification is performed using the support vector machine, the pre-training of the support vector machine can be completed by determining a penalty parameter and a kernel function.

Finally, because the head pose category of the target cattle can be determined based on a plurality of depth image frames of the target cattle's head collected at respective sampling moments, the effectiveness of the emitted gas from the target cattle and collected at this sampling moment can be marked based on the head pose category.

In the method for detecting carbon emission-involved gas from a ruminant according to the present disclosure, the depth images of the ruminant's head are collected while the emitted gas from the ruminant during eating is collected, then head poses of the ruminant during eating are classified based on an image recognition technology, so as to select, from emitted gases collected at all sampling moments, an effective emitted gas which truly reflects the actual emission amount of the carbon emission-involved gas from the ruminant, and the detection precision can be effectively improved by effectively filtering sampled gas data.

Based on the content of the above embodiment, in an optional embodiment, according to the present disclosure, after the determining image coordinates of each feature point in each distribution feature map of the feature points, the method further includes: determining, based on the image coordinates of each feature point, that the mouth of the ruminant is located in a current sampling area of the trough during eating, where the current sampling area includes a first sampling area and a second sampling area, and a distance between the first sampling area and each vent hole is less than that between the second sampling area and the vent hole; and marking effectiveness of the collected emitted gas based on the determined sampling area and the head pose category.

Figure 3:
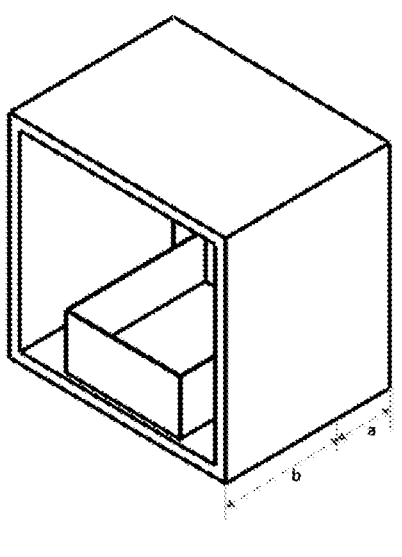
FIG. 3 is a schematic diagram showing area division of a trough according to the present disclosure.

FIG. 3 is a schematic diagram showing area division of a trough according to the present disclosure. As shown in FIG. 3, according to the present disclosure, based on a distance between the inside of the trough and vent holes formed in a side wall, an area where the entire trough is located is divided into two areas: a first sampling area (area a) and a second sampling area (area b), and the vent holes are formed in the side wall of one side of the trough close to the area a.

Based on the above division result of the area where the entire trough is located, when the above head pose category includes forwardly facing the vent holes, laterally facing the vent holes, and eating with the head down, the marking effectiveness of the collected emitted gas based on the determined sampling area and the head pose category mainly includes the following step.

The emitted gas is marked as effective when the current sampling area is the first sampling area (area a); or when the current sampling area is the second sampling area (area b), the emitted gas is marked as effective if the head pose category is forwardly facing the vent holes; or the emitted gas is marked as ineffective if the head pose category is laterally facing the vent holes or eating with the head down.

In an optional embodiment, whether the current sampling area is the first sampling area or the second sampling area is determined mainly based on whether the spatial coordinates of the mouth feature point in the five feature points coincide with spatial coordinates of the first sampling area or spatial coordinates of the second sampling area. The height direction is set to a Z-axis direction of the spatial coordinates, and whether the spatial coordinates of the mouth feature point coincide with the spatial coordinates of the first sampling area or the spatial coordinates of the second sampling area is mainly based on whether X-axis and Y-axis two-dimensional coordinates of the mouth feature point are in an X-axis and Y-axis two-dimensional coordinate area where the first sampling area or the second sampling area is located.

In conclusion, when it is determined that the current sampling area is the first sampling area, all emitted gas collected at the current moment are marked as effective (regardless of the head pose category in this case); and when it is determined that the current sampling area is the second sampling area, only the emitted gas collected when the head pose category is forwardly facing the vent holes is marked as effective, while the emitted gas collected when the head pose category is laterally facing the vent holes or eating with the head down is marked as ineffective.

In the method for detecting carbon emission-involved gas from a ruminant according to the present disclosure, on the basis of identifying and determining the head pose category of the ruminant by using the target detection model and a visual system, emitted gases are more effectively filtered with reference to the fact that the head of the ruminant is located in different areas of the trough at the current sampling moment when the emitted gases are currently collected, which can further improve the detection precision.

Based on the content of the above embodiment, in an optional embodiment, the determining, based on collected emitted gas from the ruminant during eating, an emission rate of carbon emission-involved gas in the emitted gas includes: acquiring a wind speed value in a main ventilation pipeline, a cross-sectional area of the main ventilation pipeline, and a gas temperature in the main ventilation pipeline, and acquiring a gas concentration value in the main ventilation pipeline, where the gas concentration value is measured by a gas sensor; and calculating the emission rate of the carbon emission-involved gas in the emitted gas based on the wind speed value, the cross-sectional area, the gas temperature, and the gas concentration value.

Figure 4:
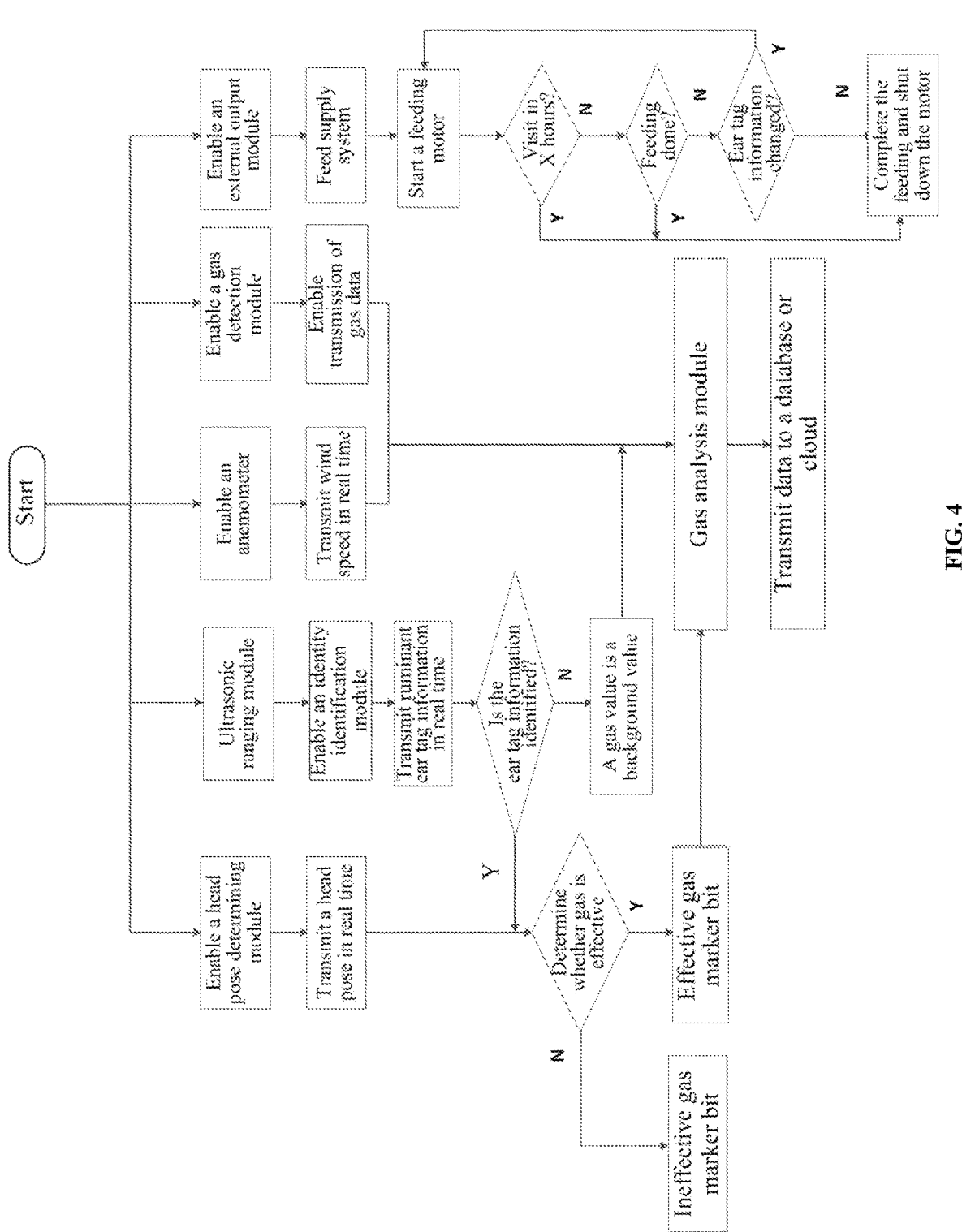
FIG. 4 is a third schematic flowchart of a method for detecting carbon emission-involved gas from a ruminant according to the present disclosure.

FIG. 4 is a third schematic flowchart of a method for detecting carbon emission-involved gas from a ruminant according to the present disclosure. As shown in FIG. 4, according to the present disclosure, a feed supply system attracts a target cattle that meets sampling requirements for eating, and the emitted gas exhaled by the target cattle is collected during eating.

In addition, an RGB-D camera is started to collect a plurality of depth image frames of the target cattle's head during eating, so as to identify a head pose category during the eating by using a target detection model based on an image recognition technology, and then the effectiveness of the collected emitted gas is marked.

Further, during collection of the emitted gas, a wind speed sensor (also referred to as an anemometer) pre-arranged in a main ventilation pipeline of a gas guiding system is used to measure the wind speed in the main ventilation pipeline during the collection of the emitted gas.

In addition, the concentration of the carbon emission-involved gas in the emitted gas is detected by a gas analysis system (mainly including a plurality of types of gas sensors).

The carbon emission-involved gas may be $CO_2$ or $CH_4$. Different gas sensors are adopted to detect different types of carbon emission-involved gases. Certainly, the contents of a plurality of a carbon emission-involved gas in the emitted gas can be obtained by simultaneously inputting the emitted gas into a plurality of types of gas sensors.

The target cattle that meets sampling requirements refers to a target cattle that has not eaten within a first preset duration and eats grass in the trough of the feed supply system for a total duration less than a second preset duration.

The present disclosure provides a ruminant carbon emission amount monitoring model, which can calculate an emission rate of a type of carbon emission-involved gas in the emitted gas based on the wind speed value in the main ventilation pipeline, the cross-sectional area of the main ventilation pipeline, the gas temperature in the main ventilation pipeline, and a gas concentration value of emission carbon emission-involved gas detected by the gas sensor, which are obtained in the above steps.

In an optional embodiment, an expression of the above ruminant carbon emission amount monitoring model is specifically as follows:

$$m = \frac{V_t \times P_0 \times S \times C}{RT} \times \mu,$$

where m is the emission rate; $V_t$ is the wind speed value; $P_0$ is a standard atmospheric pressure; S is the cross-sectional area; C is the gas concentration value; R is a gas molar constant of the carbon emission-involved gas; T is an absolute temperature corresponding to the gas temperature; and μ is gas molar mass of the carbon emission-involved gas.

The following provides a manner of deducing the expression of the above ruminant carbon emission amount monitoring model.

The mass of an carbon emission-involved gas produced by a ruminant is obtained by using an ideal gas state equation and a molar mass formula:

$$P \times V = n \times R \times T; \text{and}$$

$$n = \frac{m}{\mu},$$

where P is an air pressure in the main ventilation pipeline; V is a gas volume in the ventilation pipeline; n is the amount of gas substance in the ventilation pipeline; R is a gas molar constant; T is an absolute temperature in the main ventilation pipeline; m is the gas mass of the carbon emission-involved gas; and μ is the gas molar mass of the carbon emission-involved gas.

Further, the gas mass of the above carbon emission-involved gas may be expressed as:

$$m = \frac{PV}{RT} \times \mu.$$

Because the flow in the main ventilation pipeline can be automatically compensated for based on the temperature, but cannot be corrected based on the pressure, it is required to use the pressure to correct the gas flow in the main ventilation pipeline to obtain the actual flow $V_0$ in the main ventilation pipeline, and then the formula for calculating the emission rate of the carbon emission-involved gas in the emitted gas, i.e., the expression of the ruminant carbon emission amount monitoring model, can be derived.

After the ruminant carbon emission amount monitoring model is constructed, a emission rate of the carbon emission-involved gas in the emitted gas can be determined based on a ratio of the detected gas mass of the carbon emission-involved gas in the emitted gas to the amount n of gas substance in the ventilation pipeline.

In the method for detecting carbon emission-involved gas from a ruminant according to the present disclosure, an intelligent information technology is used, which can effectively and quickly obtain the emission rate of the carbon emission-involved gas matching the identity information of the ruminant, and can detect the carbon emission-involved gas amount from the ruminant by means of flexible manpower.

Based on the content of the above embodiment, in an optional embodiment, after the determining the emission rate of the carbon emission-involved gas in the emitted gas, the method further includes: acquiring emission rates collected at a plurality of sampling moments within a third preset duration; forming a coordinate point by each sampling moment and the emission rate collected at the sampling moment; determining a corresponding Bezier curve based on all coordinate points; and integrating emission rates of the Bezier curve within the third preset duration to obtain an emission amount of the carbon emission-involved gas in the emitted gas within the third preset duration.

In an example in which an emission rate of a carbon emission-involved gas $CO_2$ is obtained, discrete effective emission rates of $CO_2$ (x is a time point, and y is a corresponding effective emission rate of $CO_2$ at this time point) is obtained in a continuous period of time (such as a third preset duration), a Bezier curve is fitted with the obtained discrete effective emission rates of $CO_2$, and the actual emission amount of $CO_2$ in this continuous period of time is obtained.

The Bezier curve includes a starting point, an ending point, and a control point. By adjusting the control point, the shape of the curve changes, and a corresponding curve equation changes.

Figure 5:
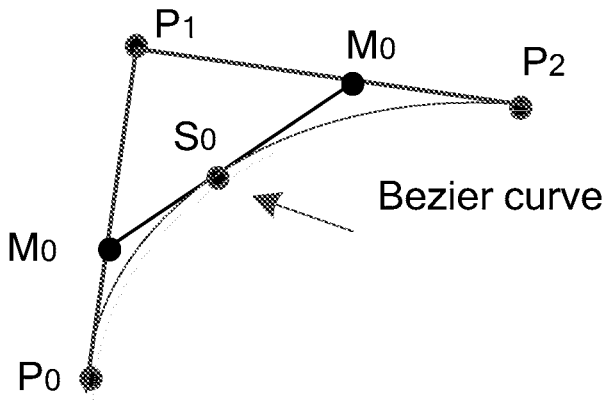
FIG. 5 is a schematic diagram of determining a Bezier curve based on emission rates collected at three sampling moments according to the present disclosure.

FIG. 5 is a schematic diagram of determining a Bezier curve based on emission rates collected at three sampling moments according to the present disclosure. As shown in FIG. 5, in an example of fitting the Bezier curve with effective emission rates of $CO_2$ collected at three different sampling moments $P_0$, $P_1$ and $P_2$, the fitted Bezier curve may be further expressed as follows:

$$y = (1-t)^2 P_0 + 2t(1-t)P_1 + t^2 P_2, t \in [0, 1]; \text{ and}$$

$$y_m = \int_{x_1}^{x_n} y.$$

By using the above formula, the emission amount of $CO_2$ actually produced by ruminants within a third preset duration can be obtained.

FIG. 6 is a schematic diagram of determining a Bezier curve based on emission rates collected at four sampling moments according to the present disclosure. As shown in FIG. 6, in an example of fitting the Bezier curve with effective emission rates of $CO_2$ collected at four different sampling moments $P_0$, $P_1$, $P_2$ and $P_3$, the fitted Bezier curve may be further expressed as follows:

$$y = P_0(1-t)^3 + 3P_1 t(1-t)^2 + 3P_2 t^2(1-t) + P_3 t^3, t \in [0, 1]; \text{ and}$$

$$y_m = \int_{x_1}^{x_n} y.$$

Therefore, the emission amount of $CO_2$ actually produced by ruminants within the third preset duration can also be calculated.

Based on the content of the above embodiment, when a plurality of sampling moments are provided, with reference to the above method, the emission amount of the carbon emission-involved gas within the entire second preset duration can be calculated by fitting a Bezier curve with the emission rates collected at a plurality of sampling points within the second preset duration.

In the method for detecting carbon emission-involved gas from a ruminant according to the present disclosure, by using a Bezier curve fitting, only the emission rates of the carbon emission-involved gas in the emitted gas from ruminants that are collected at a plurality of sampling moments within a duration are detected, so as to deduce the total emission amount of the carbon emission-involved gas from the ruminants in this duration based on the Bezier curve after linear fitting. The detection method is simple and easy to operate.

Based on the content of the above embodiment, in an optional embodiment, the method for detecting carbon emission-involved gas from a ruminant according to the present disclosure further includes: acquiring emission amounts of carbon emission-involved gas acquired within a plurality of historical sampling durations, and acquiring parameters that are collected within each of the historical sampling durations and affect a carbon emission amount; training a pre-constructed multivariable regression prediction model with the emission amount collected in each of the historical sampling durations as a dependent variable and parameters corresponding to the historical sampling durations as independent variables, to obtain a carbon emission amount prediction model; and acquiring parameters that are acquired within any sampling duration and affect the carbon emission amount, and inputting the parameters into the carbon emission amount prediction model, to predict an emission amount within the sampling duration.

The parameters affecting the carbon emission amount include ruminant species information, feed type information, feed nutrient component information, and ruminant sign and body condition information. In summary, after the carbon emission amount prediction model is obtained by pre-training the constructed multivariable regression prediction model, when the carbon emission-involved gas from ruminants is detected, the prediction of the emission amount of the carbon emission-involved gas from ruminants, which is outputted by the carbon emission amount prediction model, can be directly obtained only by only collecting relevant parameters that affect the emission amount and inputting the relevant parameters into the carbon emission amount prediction model.

The multivariable regression prediction model is a model that describes the correlation between a dependent variable and a plurality of independent variables. According to the present disclosure, a test set for pre-training a multivariable regression prediction model is pre-constructed, including parameters of multiple indexes such as ruminant species, feed types, feed nutrient components, ruminant signs and body conditions (including body weights, body sizes, etc. of individual ruminants) collected within each historical sampling duration as independent variables, and $CO_2$ emissions, $CH_4$ emissions, etc. obtained within the historical sampling duration as dependent variables. All independent variables and dependent variables collected within each historical sampling duration are used as a set of data, and the multivariate regression prediction model is iteratively pre-trained until the model passes the F test or the T test, to determine whether a regression equation of the multivariable regression prediction model has significance. If the significance meets threshold requirements, it shows that the multivariate regression prediction model is highly significant after the training, and the multivariate regression prediction model obtained in this case is used as the carbon emission amount prediction model and saved to a model management platform.

In an optional embodiment, according to the present disclosure, an expression of the multivariate regression prediction model of the $CH_4$ emission amount from ruminants is predicted based on different components in feed for the ruminants:

$$Y = \beta_0 + \beta_1 x_1 + \beta_2 x_2 + \ldots + \beta_m x_m + \varepsilon,$$

where Y represents the emission amount (in M/d) of $CH_4$, $x_1$ to $x_m$ represent m independent variables, $\beta_i$ represents a model partial regression coefficient of each independent variable, and E represents a random error.

Further, parameter estimation is implemented by using a least square method:

$$\hat{\beta} = (X^T X)^{-1} X^T y,$$

where $\hat{\beta}$ represents a regression coefficient, X represents a matrix of independent variables, and y represents a dependent variable, then an estimated value of the dependent variable y is:

$$\hat{y} = X\hat{\beta},$$

finally, the residual of the carbon emission amount prediction model may be expressed as:

$$\varepsilon = y - \hat{y} = y - X\hat{\beta}.$$

It should be added that when all the independent variables and dependent variables collected in each historical sampling duration are used as a set of training data to pre-train the multivariate regression prediction model, if the significance obtained by the F test or the T test does not meet threshold requirements, it indicates that the significance of the trained multivariate regression prediction model is low. In this case, the multivariate regression prediction model can be re-constructed, trained and tested by using a self-correction module to ensure the accuracy of the obtained carbon emission amount prediction model.

In the method for detecting carbon emission-involved gas from a ruminant according to the present disclosure, multiple information such as ruminant species, feed nutrition formulas, individual identity and body weight can be automatically recorded based on a normal feeding plan, a carbon emission amount monitoring model and a carbon emission amount prediction model of ruminants under multiple indexes are constructed, the emission amount of the emitted gas from ruminants in any period of time is obtained based on the carbon emission amount monitoring model, and the total emission amount of the carbon emission-involved gas from ruminants within a period of time is predicted based on the carbon emission amount prediction model.

Based on the content of the above embodiment, in an optional embodiment, after the acquiring parameters that are acquired within any sampling duration and affect the carbon emission amount, and inputting the parameters into the carbon emission amount prediction model, to predict an emission amount within the sampling duration, the method further includes:

adjusting, if it is determined that the emission amount within the sampling duration is greater than a preset emission amount threshold, a feed type and/or feed nutrient components, and inputting adjusted feed type information, feed nutrient component information, ruminant species information and ruminant sign and body condition information into the carbon emission amount prediction model again to predict an adjusted emission amount within the sampling duration; and iteratively performing the above steps until it is determined that the adjusted emission amount within the sampling duration is less than or equal to the preset emission amount threshold.

It should be noted that the feed fed by the feed supply system involved in the method for method for detecting carbon emission-involved gas from a ruminant according to the present disclosure may be an attractant, which is different from feed normally fed to ruminants and is mainly used to lure ruminants to eat the attractant in the trough of the feed supply system after the ruminants eat the feed normally. And the method detects the emission rate of the carbon emission-involved gas in the emitted gas when the ruminants eat the attractant.

Then, based on the comparison between the emission rate of the carbon emission-involved gas and a preset emission amount threshold, whether the carbon emission-involved gas generated exceeds the standard is determined under the impact of parameters affecting the carbon emission amount, i.e., the feed type and/or feed nutrient components of the feed which has been eaten by a ruminant and species information and sign and body condition information of the ruminant.

If it is determined that the carbon emission-involved gas has exceeded the standard, then guiding may be provided to properly adjust the feed type and/or feed nutritional components for normal feeding (the species information and the sign and body condition information cannot be adjusted), to reduce the emission rate of the carbon emission-involved gas.

Therefore, in the method for detecting carbon emission-involved gas from a ruminant according to the present disclosure, various feed types and/or feed nutrient components can be accurately tested by means of big data acquisition, and the emission rate of the carbon emission-involved gas from the fed ruminants with different species and different signs and body conditions can be detected, thus providing a basis for assisting the filtering of low-carbon species and low-carbon feed.

Based on the content of the above embodiment, in an optional embodiment, before the determining the emission rate of the carbon emission-involved gas in the emitted gas, the method further includes: setting parameters of a robust filter to calibrate the gas sensor by using the air collected when no ruminant eats.

As shown in FIG. 4, since $CO_2$ and $CH_4$ contained in the air have a certain impact on the detection of emission amounts of $CO_2$ and $CH_4$ produced by ruminants, an air background denoising method needs to be constructed to obtain $CO_2$ and $CH_4$ actually produced by ruminants, so as to provide a basis for subsequent data analysis.

On the basis of ensuring that there are no ruminants such as cattle and sheep around the apparatus for detecting carbon emission-involved gas from a ruminant (in this case, no ear tag information is detected), the gas sensor in the gas analysis system (also referred to as a gas analysis module) is first calibrated by using standard gas, and then through a sensor technology by the calibrated gas sensor, parameters such as $CO_2$ gas and $CH_4$ gas in the air are subjected to steps such as signal conditioning, sampling, quantization and coding and are transmitted to the controller for data processing and analysis to obtain a gas collection value.

Due to the complexity and off-line irregularity of the gas collection value obtained under the ruminant-free background, a robust filtering algorithm can be used for processing, and its specific implementation algorithm is as follows.

In a dynamic system, system noise and observation noise are used as random signals with limited energy, respectively, where the system noise W (k) is regarded as a random signal with limited energy, namely:

$$\sum_{0}^{k} \|W(k)\| < \infty, \text{ and}$$

the observation noise V (k) is used as a random signal with limited energy, namely:

$$\sum_{0}^{k} \|V(k)\| < \infty.$$

The core of robust filtering is to arrange a filter, so that a norm in a closed-loop transfer function from system interference to an estimation error is less than a given positive number, and the filtering error system gradually stabilizes and meets the requirements. In this case, an average value after filtering is an air background average value.

In the method for detecting carbon emission-involved gas from a ruminant according to the present disclosure, the gas sensor detects an indoor environment and the concentration of the gas exhaled by ruminants, and by using the air background denoising method, the emission rate of the carbon emission-involved gas in the emitted gas actually exhaled by ruminants is recorded in real time, and the detection result is more accurate.

FIG. 7 is a schematic structural diagram of an apparatus for monitoring a carbon emission amount from a ruminant according to the present disclosure. As shown in FIG. 7, the apparatus mainly includes a data acquisition unit 701, an operation control unit 702, and an emission rate detection unit 703.

The data acquisition unit 701 is mainly configured to continuously receive ear tag information of the ruminant that is collected by an identity information identification module in a monitoring range.

The operation control unit 702 is mainly configured to determine an operation state of a feed supply system based on the ear tag information.

The emission rate detection unit 703 is mainly configured to determine, based on collected emitted gas from the ruminant during eating, an emission rate of carbon emission-involved gas in the emitted gas when it is determined that the feed supply system is in a continuous operation state.

In the apparatus for detecting carbon emission-involved gas from a ruminant according to the present disclosure, the ear tag information of the ruminant is detected to determine whether there is a ruminant in a detection area and feeding information of the ruminant, then the operation state of the feed supply system is controlled, and an intelligent information technology is used to acquire the emission rate of the carbon emission-involved gas matching the identity of the ruminant, which can detect the carbon emission-involved gas amount from the ruminant by means of flexible manpower.

It should be noted that the apparatus for detecting carbon emission-involved gas from a ruminant according to the embodiment of the present disclosure can perform the method for detecting carbon emission-involved gas from a ruminant according to any of the above embodiments during specific operation, which will not be described in detail in this embodiment.

FIG. 8 is a front view of an apparatus for monitoring a carbon emission amount from a ruminant according to the present disclosure. As shown in FIG. 8, the apparatus mainly includes: an identity information identification module (such as an RFID reader 5), a feed supply system 1, a gas guiding system 2, and a gas analysis system 3.

The feed supply system 1 includes a trough 11 and a quantitative feeder 12, where an output end of the quantitative feeder 12 is connected to the trough 11 through a discharge pipe 13, and a side edge of the trough 11 is provided with vent holes 14. The gas guiding system 2 mainly includes a main ventilation pipeline 21 and a sampling pipeline 22; an air inlet end of the main ventilation pipeline 21 is connected to the vent holes of the trough 11, and a fan 23 is arranged in the main ventilation pipeline; and when the fan 23 is running, negative pressure is formed in the main ventilation pipeline, so as to guide the gas at the vent holes of the trough 11 into the main ventilation pipeline 21. The sampling pipeline 22 is in connection with the main ventilation pipeline 21 and the gas analysis system 3 to sample the gas in the main ventilation pipeline 21 to the gas analysis system 3. The gas analysis system 3 mainly includes a gas sensor.

The system carbon emission-involved gas further includes a processor; and the processor includes the apparatus for detecting carbon emission-involved gas from a ruminant according to the above embodiment.

FIG. 9 is a left view of an apparatus for monitoring a carbon emission amount from a ruminant according to the present disclosure. As shown in FIG. 9, the apparatus for monitoring a carbon emission amount from a ruminant according to the present disclosure further includes a main body structure 7, and the trough 11 is fixedly placed in an internal space of the main body structure 7. When the carbon emission amount is monitored, the feed in a feed box is put into the trough 11 through the quantitative feeder 12, and ruminants are attracted to the monitoring apparatus by the feed to eat from the trough 11.

According to the present disclosure, the shape of the trough 11 as a feed container is not specifically limited, but many vent holes 14 are formed in a side edge of the trough 11.

Optionally, the trough 11 may be made into a tapered funnel-shaped structure with a trapezoidal longitudinal section, many vent holes 14 are formed in an internal space of the trough 11 in the main body structure 7 and close to the inner side edge, and an output end of the quantitative feeder 12 is connected to the inner side edge of the trough 11 through a discharge pipe 13. When the feed is fed, most of the feed is located close to the inner side edge. Considering that the feed may block the vent holes 14, the vent hole 14 are formed only in the upper half of the inner side edge, so that it can be ensured that the vent holes 14 formed in the upper half of the side edge will not be blocked by the feed when the feed feeding speed is low and ruminants continuously eat.

Further, an air inlet of the main ventilation pipeline 21 in the gas guiding system 2 is connected to the above side edge of the trough 11 provided with the vent holes 14, and it is preferable that all the vent holes 14 are covered by the air inlet of the main ventilation pipeline 21. When the feed is fed to attract ruminants to eat from the trough 11, since the feed is mainly distributed close to the side provided with the vent holes 14, the snout of the ruminant are as close as possible to the vent holes 14. In addition, because the fan 23 arranged in the main ventilation pipeline is turned on and negative pressure is formed in the main ventilation pipeline, the gas exhaled by the ruminant is introduced into the main ventilation pipeline 21 from the vent holes 14.

As shown in FIG. 8, one end of the sampling pipeline 22 is in connection with the main ventilation pipeline 21, and the other end thereof is connected to an input end of the gas analysis system 3, so that the gas in the main ventilation pipeline 21 can be introduced, through the sampling pipeline 22, to the gas analysis system for carbon emission amount detection.

In an optional embodiment, the gas analysis system according to the present disclosure mainly uses gas sensors to detect the carbon emission amount. Specifically, the gas introduced by the sampling pipeline 22 may be injected into a test box first, and then diverted to each parallel pipeline, so that the gas can be introduced through each parallel pipeline to different types of gas sensors for detection of different concentrations of gases mainly including $CH_4$, $CO_2$, etc.

In an optional embodiment, each of the above gas sensors may be constructed based on a terahertz sensor array, and each gas sensor is connected to the parallel pipeline in a pluggable manner, which facilitates independent replacement based on actual detection needs.

In the system for monitoring a carbon emission amount from a ruminant according to the present disclosure, a ruminant can be induced to visit the system many times a day by means of the feed supply system, its exhaled metabolic gas is collected by means of the gas guiding system during eating, and the collected metabolic gas is conveyed to the gas analysis system, so that the carbon emission amount in the metabolic gas can be detected by the gas analysis system, and the metabolic gas from the ruminant can be effectively monitored and accurately measured.

Based on the content of the above embodiment, in an optional embodiment, a first air filter 24 is arranged in the main ventilation pipeline; the first air filter is located between an air inlet end of the main ventilation pipeline and the fan 23; and a perforated plate 25 is laid at a joint between an output end of the first air filter 24 and the main ventilation pipeline 21.

As shown in FIG. 8, the gas exhaled by a ruminant and collected from the trough 11 necessarily contains more impurities such as fine feed and water vapor, which will affect the monitoring precision to some extent. In view of this, according to the present disclosure, the flowing gas is filtered by adding the first air filter 24 in the main ventilation pipeline.

In an optional embodiment, the first air filter 24 may be arranged close to the air inlet end of the main ventilation pipeline.

Further, because of the action of the fan, the gas flow velocity in the main ventilation pipeline 21 is unstable, and the first air filter 24 also affects the gas flow velocity in the main ventilation pipeline 21, which is not conducive to the smooth sampling of the gas into the gas analysis system 3 through the sampling pipeline. In view of this, according to the present disclosure, a perforated plate 25 is arranged at the output end of the first air filter 24, so that the gas flowing through the perforated plate 25 can flow steadily.

Further, the system for monitoring a carbon emission amount from a ruminant according to the present disclosure may further include a wind speed sensor 26, where a probe of the wind speed sensor 26 is arranged in the main ventilation pipeline 21, and may be specifically arranged between the first air filter 24 and the fan 23, so as to monitor the gas flow velocity in the main ventilation pipeline 21 in real time.

According to the present disclosure, a perforated plate 25 is arranged at the output end of the first air filter 24 to stabilize the flowing of the flowing gas, and the accuracy of the gas flow velocity monitored by the wind speed sensor 26 can also be ensured.

Further, according to the present disclosure, a sampling air pump may be added in the sampling pipeline 22, which can facilitate the sampling of the gas in the main ventilation pipeline to the gas sensor 3 through the sampling pipeline, and further improve the monitoring precision.

In order to further filter out the feed residue or water vapor, etc. that causes interference to monitoring results from the sampled gas, a second air filter may be arranged in the sampling pipeline 22.

FIG. 10 is a schematic structural diagram of relevant components of a main ventilation pipeline in a gas guiding system according to the present disclosure. As shown in FIG. 10, after the above components are sequentially connected along a gas flow direction in the main ventilation pipeline 21, the collected gas exhaled by ruminants has the following flow direction.

The air inlet end of the main ventilation pipeline 21 is connected to the vent holes 14 of the trough 11; after the fan 23 arranged at an air outlet end of the main ventilation pipeline 21 is turned on, the gas exhaled by a ruminant enters the main ventilation pipeline 21 through the vent holes 14, then flows through the first air filter 24 for preliminary filtration, flows stably by means of the perforated plate 25, and then flows through the probe of the wind speed sensor 26, so as to especially detect the flow velocity of the gas in the main ventilation pipeline 21; and then, a part of the gas is sampled to the gas analysis system through the sampling pipeline 22, so that the content of a target gas (such as $CH_4$ or $CO_2$) in the sampled gas can be detected by the gas sensor, and the rest of the gas is discharged by the fan.

FIG. 11 is a partial schematic structural diagram of a quantitative feeder according to the present disclosure. As shown in FIG. 11, the quantitative feeder 12 according to the present disclosure mainly includes a feed box 121, and a discharger 122 connected to a lower opening of the feed box 121, where the feed box 121 is configured to centrally store feed to be fed, and a discharge port of the discharger 122 is in connection with the discharge pipe 13, so that the feed outputted by the discharger 122 is introduced into the trough 11 through the discharge pipe 13.

FIG. 12 is a schematic structural diagram of a discharger according to the present disclosure. As shown in FIG. 12, the discharger 122 mainly includes a discharger housing 1221 and distributing gear teeth 1222 located inside the discharger housing 1221.

An upper end of the discharger housing 1221 is configured with a feeding hole, the feed box 121 is fixedly arranged on the discharger housing 1221, and a lower opening of the feed box 121 is connected to the feeding hole configured in the discharger housing 1221.

Further, multiple material accommodating grooves are configured along an outer circumference of the distributing gear teeth 1222 in an array. As shown in FIG. 12, there are six material accommodating grooves in the distributing gear teeth 1222, and the outer circumference of the distributing gear teeth is in clearance fit with the discharger housing. The distributing gear teeth 1222 are driven by the stepping motor to rotate, so that the feed in the feed box 121 flows in when any material accommodating groove rotates to the feeding hole, and when the material accommodating groove rotates to the discharge port connected to the discharge pipe 13, the injected feed is injected into the trough 11 through the discharge pipe 13.

It should be noted that whether the feed is put into the trough 11 may be controlled by controlling the on-off of the stepping motor, and the amount of the feed put into the trough 11 within each duration may be controlled by controlling the rotation speed of the stepping motor.

FIG. 13 is a schematic structural diagram of a power supply system according to the present disclosure. As shown in FIG. 13, the power supply system 4 of the system for monitoring a carbon emission amount from a ruminant according to the present disclosure mainly includes a storage battery 41, a switching power supply 42, a power switching module 43, and a power conversion module 44.

The storage battery 41 may be connected to a solar charging module, and the solar charging module mainly includes a solar charging controller 46 and a solar cell panel 47. The solar cell panel 47 is configured to convert solar energy into electric energy, and is controlled by the solar charging controller 46, and the obtained electric energy is stored in the storage battery 41.

Further, the power switching module 43 switches the connection of the storage battery 41 and the switching power supply 42; and the power conversion module 44 adjusts connected voltages of the storage battery 41 and the switching power supply 42.

The power supply system 4 according to the present disclosure can provide power by means of the storage battery 41 or the switching power supply 42 (such as an industrial switching power supply), and the two power supply manners can ensure that the provided system for monitoring a carbon emission amount from the ruminant can have a long-term endurance even if the system is put into outdoor use.

Based on the content of the above embodiment, in an optional embodiment, as shown in FIG. 8, a main control module, an RFID reader 5 and an ultrasonic ranging module 6 are further added to the system for monitoring a carbon emission amount from a ruminant according to the present disclosure.

FIG. 14 is a schematic diagram showing a connection between a main control module and other components according to the present disclosure. As shown in FIG. 14, a signal output end of the RFID reader 5 and a signal output end of the ultrasonic ranging module 6 are connected to a signal input end of the main control module.

The signal output end of the main control module is connected to a controller of the stepping motor, a controller of the fan, and a controller of the sampling air pump.

In an optional embodiment, the apparatus for monitoring a carbon emission amount from the ruminant according to the present disclosure mainly includes a control module, an RFID reader 5, an ultrasonic ranging module 6, a gas guiding system 2, a gas analysis system 3, an external output module, a local control module, a remote control module, etc.

The RFID reader 5 mainly uses an RFID technology to identify ear tag information of a ruminant to obtain identity information of the ruminant. The RFID reader 5 may be arranged in the internal space of the main body structure 7, and its collection range covers an area where the trough is located. If the RFID reader 5 can detect the ear tag information, it indicates that there is a ruminant around the system for monitoring a carbon emission amount from a ruminant in this case; and if the RFID reader 5 does not detect the ear tag information, it indicates that there is no ruminant around the system for monitoring a carbon emission amount from a ruminant in this case. A detection result of the RFID reader 5 is uploaded to the control module, and the control module can control, based on whether there is a ruminant around the system for monitoring a carbon emission amount from a ruminant, operation states (including on/off and/or rotation speeds) of the external output module including the stepping motor, the fan, and the sampling air pump.

The ultrasonic ranging module is mainly configured to detect a distance between the head of the ruminant and the ultrasonic ranging sensor in real time, and upload the detected distance information to the control module; if the control module determines that the distance is excessive (greater than a preset threshold), a detection result obtained based on the currently collected gas is considered as an ineffective detection result, while only a gas detection result collected when the distance between the head of ruminant and the ultrasonic ranging sensor is within the preset range is used as an effective detection result.

In an optional embodiment, a head pose determining module may be further added to the system for detecting a carbon emission-involved gas amount from a ruminant according to the present disclosure, and a signal output end of the head pose determining module is connected to a signal input end of the main control module.

The head pose determining module mainly includes an RGB-D camera. Head color depth images of a ruminant are photographed by means of the RGB-D camera, and the head color depth images are inputted into a pre-trained target detection model, so that three-dimensional spatial coordinates of several key points (such as the ears, the eyes, and the mouth) of the head of the ruminant in the trough 11 can be obtained. Then, the main control module can determine, based on the three-dimensional spatial coordinates, whether the head pose of the ruminant meets needs for effectively collecting an exhaled gas.

Based on the content of the above embodiment, in an optional embodiment, as shown in FIG. 8, the system for monitoring a carbon emission amount from a ruminant according to the present disclosure may further include a body weight collection platform 9, where the body weight collection platform 9 is arranged in front of the feed supply system 1, and can collect body weight information of a ruminant when the ruminant stands on the body weight collection platform 9 and eats from the trough 11.

As shown in FIG. 14, a signal output end of the body weight collection platform 9 is connected to a signal input end of the main control module to send the collected body weight information of the ruminant to the main control module in real time. The main control module can determine, with reference to the detected body weight information, whether there is a ruminant around the provided system for monitoring a carbon emission amount from a ruminant.

In addition, a user may also use the body weight information displayed by the main control module and the contents of $CO_2$ and $CH_4$ in the gas detected by the gas analysis system 3 to provide data support for accurate analysis of the carbon emission amount from the ruminant.

Based on the content of the above embodiment, in an optional embodiment, as shown in FIG. 8, the system for monitoring a carbon emission amount from a ruminant according to the present disclosure may further include a sign collection and detection unit 10, where the sign collection and detection unit is arranged on a side of the body weight collection platform to collect sign information of the ruminant.

As shown in FIG. 14, a signal output end of the sign collection and detection unit 10 is connected to the signal input end of the main control module.

Accordingly, a user may also use the sign information displayed by the main control module and the contents of $CO_2$ and $CH_4$ in the gas detected by the gas analysis system 3 to provide data support for accurate analysis of the carbon emission amount of the ruminant.

FIG. 15 is a schematic structural diagram of a system for monitoring a carbon emission amount from a ruminant according to the present disclosure. With reference to the contents shown in FIGS. 14 and 15, in the system for monitoring a carbon emission amount from a ruminant according to the present disclosure, each main control module is in communication and connection with a local control module and a remote communication module.

The local control module is mainly configured to display the concentration values of gases such as $CO_2$ and $CH_4$ detected by the gas analysis system 3 and the wind speed, temperature value, etc. in the main ventilation pipeline of the gas guiding system in real time, and store all the detection results in a local database.

Further, the remote communication module of each system for monitoring a carbon emission amount from a ruminant uses a long range radio (LORA) Internet of Things gateway technology to transmit the collected detection results to an information management platform on a personal computer (PC), so that the user can remotely control each system for monitoring a carbon emission amount from a ruminant and save the transmitted detection results in the cloud.

FIG. 16 is a schematic structural diagram of an electronic device according to the present disclosure. As shown in FIG. 16, the electronic device may include a processor 1610, a communication interface 1620, a memory 1630, and a communication bus 1640, where the processor 1610, the communication interface 1620 and the memory 1630 communicate with one another by means of the communication bus 1640. The processor 1610 may invoke logic instructions in the memory 1630 to perform the method for detecting carbon emission-involved gas from a ruminant. The method includes: continuously receiving ear tag information of the ruminant that is collected by an identity information identification module in a monitoring range; determining an operation state of a feed supply system based on the ear tag information; and determining, based on collected emitted gas from the ruminant during eating, an emission rate of carbon emission-involved gas in the emitted gas when it is determined that the feed supply system is in a continuous operation state.

Besides, the logic instructions in the memory 1630 may be implemented as a software function unit and may be stored in a computer-readable storage medium when sold or used as a separate product. Based on such understanding, the technical solutions of the present disclosure essentially or the part contributing to the prior art or part of the technical solution may be implemented in a form of a software product. The computer software product may be stored in a storage medium, and includes several instructions for enabling a computer device (which may be a personal computer, a server, a network device, or the like) to perform all or some steps of the method according to each of the embodiments of the present disclosure. The foregoing storage medium includes any medium that can store a program code, such as a universal serial bus (USB) flash disk, a mobile hard disk, a read-only memory (ROM), a random access memory (RAM), a magnetic disk, or an optical disk.

According to another aspect, the present disclosure further provides a computer program product, where the computer program product includes a computer program stored on a non-transient computer-readable storage medium, the computer program includes program instructions, and when the program instructions are executed by a computer, the computer can perform the method for detecting carbon emission-involved gas from a ruminant according to the methods described above. The method includes: continuously receiving ear tag information of the ruminant that is collected by an identity information identification module in a monitoring range; determining an operation state of a feed supply system based on the ear tag information; and determining, based on collected emitted gas from the ruminant during eating, an emission rate of carbon emission-involved gas in the emitted gas when it is determined that the feed supply system is in a continuous operation state.

According to still another aspect, the present disclosure further provides a non-transient computer-readable storage medium storing a computer program thereon, where the computer program, when executed by a processor, implements the method for detecting carbon emission-involved gas from a ruminant according to each of the embodiments described above. The method includes: continuously receiving ear tag information of the ruminant that is collected by an identity information identification module in a monitoring range; determining an operation state of a feed supply system based on the ear tag information; and determining, based on collected emitted gas from the ruminant during eating, an emission rate of carbon emission-involved gas in the emitted gas when it is determined that the feed supply system is in a continuous operation state.

The apparatus embodiment described above is merely schematic, where the unit described as a separate component may or may not be physically separated, and a component displayed as a unit may or may not be a physical unit, that is, the component may be located at one place, or distributed on multiple network units. Some or all of the modules may be selected based on actual needs to achieve the objectives of the solutions of the embodiments. A person of ordinary skill in the art can understand and implement the embodiments without creative efforts.

Through the description of the foregoing implementations, a person skilled in the art can clearly understand that the implementations can be implemented by means of software plus a necessary universal hardware platform, or certainly, can be implemented by hardware. Based on such understanding, the technical solutions essentially or the part contributing to the prior art may be implemented in a form of a software product. The computer software product may be stored in a computer-readable storage medium such as a ROM/RAM, a magnetic disk, or an optical disk, and includes several instructions for enabling a computer device (which may be a personal computer, a server, a network device, or the like) to execute the method according to each of the embodiments or parts of the embodiments.

Finally, it should be noted that the foregoing embodiments are only used to illustrate the technical solutions of the present disclosure, and are not intended to limit the present disclosure. Although the present disclosure is described in detail with reference to the foregoing embodiments, a person of ordinary skill in the art should understand that he/she can still modify the technical solutions described in the foregoing embodiments, or make equivalent substitutions to some technical features therein. These modifications or substitutions do not make the essence of the corresponding technical solutions depart from the spirit and scope of the technical solutions in the embodiments of the present disclosure.

What is claimed is:

1. A method for detecting carbon emission-involved gas from a ruminant, comprising:
   continuously receiving ear tag information of the ruminant that is collected by an identity information identification module in a monitoring range;
   determining an operation state of a feed supply system based on the ear tag information; and
   determining, based on collected emitted gas from the ruminant during eating, an emission rate of carbon emission-involved gas in the emitted gas when it is determined that the feed supply system is in a continuous operation state, wherein the determining an operation state of a feed supply system based on the ear tag information comprises:
      determining identity information of the ruminant based on the ear tag information;
      querying for a historical eating record of the ruminant from a target database based on the identity information;

controlling the feed supply system to switch from a stop state to the continuous operation state so as to supply feed into a trough, if it is determined based on the historical eating record that the ruminant has not eaten within a first preset duration before a current moment;

counting an operation duration of the feed supply system;

controlling the feed supply system to switch from the continuous operation state to the stop state when it is determined that the operation duration has reached a second preset duration and/or the identity information identification module has not collected the ear tag information; and controlling the feed supply system to keep in the stop state if it is determined based on the historical eating record that the ruminant has eaten within the first preset duration before the current moment, wherein the stop state refers to a state in which a quantitative feeder is stopped, and does not put feed in a feed box into the trough; and the continuous operation state refers to a state in which the quantitative feeder puts the feed in the feed box into the trough in a preset mode, wherein before the determining, based on collected emitted gas from the ruminant during eating, an emission rate of carbon emission-involved gas in the emitted gas, the method further comprises:

acquiring a plurality of depth image frames of the ruminant's head during eating collected by an RGB-D camera;

inputting each depth image frame into a pre-trained target detection model to obtain a distribution feature map of feature points outputted by the target detection model;

determining image coordinates of each feature point in each distribution feature map of the feature points, and converting the image coordinates of the feature point into spatial coordinates with the RGB-D camera as a coordinate origin, to obtain a feature point spatial coordinate data set, wherein the feature points comprise binaural feature points, binocular feature points and a mouth feature point of the ruminant;

classifying, based on a support vector machine, spatial position relationships between all spatial coordinates in the feature point spatial coordinate data set and vent holes on the trough, and determining a head pose category of the ruminant relative to the trough; and marking effectiveness of the collected emitted gas based on the head pose category, wherein the vent holes are configured in the trough to collect the emitted gas, wherein the target detection model is obtained by training a basic network model by using a plurality of depth image samples of the ruminant's head and a distribution feature map label corresponding to each of the depth image samples; and the basic network model is generated based on ResNet as a basic network structure through replacing a classification layer of the ResNet with a deconvolution layer.

2. The method according to claim 1, wherein after the determining image coordinates of each feature point in each distribution feature map of the feature points, the method further comprises:

determining, based on the image coordinates of each feature point, that a mouth of the ruminant is located in a current sampling area of the trough during eating, wherein the current sampling area comprises a first sampling area and a second sampling area, and a distance between the first sampling area and each vent hole is less than that between the second sampling area and the vent hole; and marking effectiveness of the collected emitted gas based on the determined sampling area and the head pose category.

3. The method according to claim 2, wherein the head pose category comprises forwardly facing the vent holes, laterally facing the vent holes, and eating with the head down; and the marking effectiveness of the collected emitted gas based on the determined sampling area and the head pose category comprises:

marking the emitted gas as effective when the current sampling area is the first sampling area;

marking the emitted gas as effective if the head pose category is forwardly facing the vent holes when the current sampling area is the second sampling area; and marking the emitted gas as ineffective if the head pose category is laterally facing the vent holes or eating with the head down.

4. The method according to claim 3, wherein after the determining the emission rate of the carbon emission-involved gas in the emitted gas, the method further comprises:

acquiring emission rates collected at a plurality of sampling moments within a third preset duration;

forming a coordinate point with each sampling moment and an emission rate collected at the sampling moment;

determining a corresponding Bezier curve based on all coordinate points; and integrating emission rates of the Bezier curve within the third preset duration to obtain an emission amount of the carbon emission-involved gas in the emitted gas within the third preset duration.

5. The method according to claim 2, wherein after the determining the emission rate of the carbon emission-involved gas in the emitted gas, the method further comprises:

acquiring emission rates collected at a plurality of sampling moments within a third preset duration;

forming a coordinate point with each sampling moment and an emission rate collected at the sampling moment;

determining a corresponding Bezier curve based on all coordinate points; and integrating emission rates of the Bezier curve within the third preset duration to obtain an emission amount of the carbon emission-involved gas in the emitted gas within the third preset duration.

6. The method according to claim 1, wherein the determining, based on collected emitted gas from the ruminant during eating, an emission rate of carbon emission-involved gas in the emitted gas comprises:

acquiring a wind speed value in a main ventilation pipeline, a cross-sectional area of the main ventilation pipeline, and a gas temperature in the main ventilation pipeline, and acquiring a gas concentration value in the main ventilation pipeline, wherein the gas concentration value is measured by a gas sensor; and calculating the emission rate of the carbon emission-involved gas in the emitted gas based on the wind speed value, the cross-sectional area, the gas temperature, and the gas concentration value.

7. The method according to claim 6, wherein a calculation formula for calculating the emission rate of the carbon emission-involved gas in the emitted gas based on the wind speed value, the cross-sectional area, the gas temperature, and the gas concentration value is as follows:

$$m = \frac{V_t \times P_0 \times S \times C}{RT} \times \mu,$$

wherein m is the emission rate; $V_t$ is the wind speed value; $P_0$ is a standard atmospheric pressure; S is the cross-sectional area; C is the gas concentration value; R is a gas molar constant of the carbon emission-involved gas; T is an absolute temperature corresponding to the gas temperature; and $\mu$ is gas molar mass of the carbon emission-involved gas.

8. The method according to claim 6, wherein after the determining the emission rate of the carbon emission-involved gas in the emitted gas, the method further comprises:

acquiring emission rates collected at a plurality of sampling moments within a third preset duration;

forming a coordinate point with each sampling moment and an emission rate collected at the sampling moment;

determining a corresponding Bezier curve based on all coordinate points; and integrating emission rates of the Bezier curve within the third preset duration to obtain an emission amount of the carbon emission-involved gas in the emitted gas within the third preset duration.

9. The method according to claim 6, wherein before the determining the emission rate of the carbon emission-involved gas in the emitted gas, the method further comprises:

setting parameters of a robust filter to calibrate the gas sensor by using air collected when no ruminant eats.

10. The method according to claim 1, wherein after the determining the emission rate of the carbon emission-involved gas in the emitted gas, the method further comprises:

acquiring emission rates collected at a plurality of sampling moments within a third preset duration;

forming a coordinate point with each sampling moment and an emission rate collected at the sampling moment;

determining a corresponding Bezier curve based on all coordinate points; and integrating emission rates of the Bezier curve within the third preset duration to obtain an emission amount of the carbon emission-involved gas in the emitted gas within the third preset duration.

11. The method according to claim 10, further comprising:

acquiring emission amounts of carbon emission-involved gas acquired within a plurality of historical sampling durations, and acquiring parameters that are collected within each of the historical sampling durations and affect a carbon emission amount;

training a pre-constructed multivariate regression prediction model with an emission amount collected in each historical sampling duration as a dependent variable and parameters corresponding to the historical sampling duration as independent variables, to obtain a carbon emission amount prediction model; and acquiring parameters that are acquired within any sampling duration and affect the carbon emission amount, and inputting the parameters into the carbon emission amount prediction model, to predict an emission amount within the sampling duration, wherein the parameters affecting the carbon emission amount comprise ruminant species information, feed type information, feed nutrient component information, and ruminant sign and body condition information.

12. The method according to claim 11, wherein after the acquiring parameters that are acquired within any sampling duration and affect the carbon emission amount, and inputting the parameters into the carbon emission amount prediction model, to predict an emission amount within the sampling duration, the method further comprises:

adjusting, if it is determined that the emission amount within the sampling duration is greater than a preset emission amount threshold, a feed type and/or feed nutrient components;

inputting adjusted feed type information, feed nutrient component information, ruminant species information and ruminant sign and body condition information into the carbon emission amount prediction model again to predict an adjusted emission amount within the sampling duration; and iteratively performing the above steps until it is determined that the adjusted emission amount within the sampling duration is less than or equal to the preset emission amount threshold.

13. An electronic device, comprising a memory, a processor, and a computer program stored in the memory and executable on the processor, wherein the computer program, when executed by the processor, implements the method for detecting carbon emission-involved gas from a ruminant according to claim 1.

\*   \*   \*   \*   \*